US008512820B2

(12) United States Patent
Zhang et al.

(10) Patent No.: US 8,512,820 B2
(45) Date of Patent: Aug. 20, 2013

(54) ORGANIC IONIC PHENYLPYRIMIDINE COMPOUNDS AND DISPLAYS FORMED THEREOF

(75) Inventors: Yongqiang Zhang, Longmont, CO (US); Su Yang, Longmont, CO (US)

(73) Assignee: Citizen Finetech Miyota Co., Ltd., Nagano (JP)

( * ) Notice: Subject to any disclaimer, the term of this patent is extended or adjusted under 35 U.S.C. 154(b) by 64 days.

(21) Appl. No.: 13/160,175

(22) Filed: Jun. 14, 2011

(65) Prior Publication Data

US 2012/0319044 A1   Dec. 20, 2012

(51) Int. Cl.
| | |
|---|---|
| *C09K 19/34* | (2006.01) |
| *C07D 239/02* | (2006.01) |
| *C07D 239/10* | (2006.01) |
| *C07D 239/24* | (2006.01) |
| *C07D 239/34* | (2006.01) |
| *C07D 239/38* | (2006.01) |
| *C07F 9/54* | (2006.01) |

(52) U.S. Cl.
USPC ....... 428/1.1; 252/299.61; 544/242; 544/243; 544/298; 544/315; 544/316; 544/318; 544/335

(58) Field of Classification Search
USPC ................ 544/242, 298, 315, 316, 318, 335, 544/243; 252/299.61; 428/1.1
See application file for complete search history.

(56) References Cited

U.S. PATENT DOCUMENTS

| | | |
|---|---|---|
| 2002/0180925 A1 | 12/2002 | Tsuboyama et al. |
| 2005/0253983 A1 | 11/2005 | Carson et al. |
| 2006/0011887 A1 | 1/2006 | Kato et al. |

*Primary Examiner* — Shean C Wu

(57) ABSTRACT

Ionic mesogenic compounds of formula (I) can be used to form liquid crystal displays, such as ferroelectric liquid crystal displays, having enhanced anti-image sticking properties. The mesogenic compounds may contain a cationic group such as an ammonium or phosphonium group bonded to an alkyl chain that is terminally bonded to a para-substituted pyrimidyl benzene moiety. The counterion can be an organic or inorganic anion. The compounds can be used either as dopants in art ferroelectric liquid crystal compositions to reduce image sticking, or can be used as the primary or predominant component of a liquid crystal display system. Additional compounds, devices, and methods are disclosed.

45 Claims, 6 Drawing Sheets

ORGANIC IONIC PHENYLPYRIMIDINE COMPOUNDS AND DISPLAYS FORMED THEREOF

BACKGROUND

Ferroelectric liquid crystal displays offer great advantages in terms of quick response, the time needed for a change in orientation of the ferroelectric liquid crystal array being much shorter than the time needed for the change in a typical nematic liquid crystal. One advantage of this quick response is that sequential coloring of pixels is possible at a refresh rate that facilitates color fusion, that is, the appearance to the human eye of the pixel as a single color rather than as rapidly sequentially changing colors. Sequential color also enables greater resolution for a particular pixel size, as a single pixel can display all colors, rather than requiring three pixels, red, green and blue, to display a full color spectrum.

One phenomenon of liquid crystal displays, such as those of the ferroelectric type, is termed "image sticking" (also known as "optical hysteresis" or "ghost images"), referring to a residual image that is displayed on the screen persisting long after the driving voltages are removed from the ferroelectric liquid crystal (FLC) pixels. Charge densities are especially high in FLC devices because of the spontaneous polarization and the resulting internal electric fields. In sequential color ferroelectric liquid crystal on silicon (FLCOS) devices, a DC offset in the drive algorithm may cause severe sticking, but operation in a DC balanced mode can reduce image sticking. DC balancing refers to the process wherein a voltage of inverse polarity is applied to a liquid crystal pixel immediately following application of a display voltage to assist in neutralizing residual electrical charges that may be responsible for image sticking. However, this mode of operation turns off the LEDs supplying the light modulated by the FLCs during the balance phase when the inverse polarity voltage is applied, thereby reducing the light output of the device. For more information, see U.S. Pat. No. 6,075,577, incorporated herein by reference in its entirety.

Images are produced on an FLC display by applying a suitable pattern of voltages to the display's pixels and viewing the resultant pattern of FLC optical states using crossed polarizers. In standard video systems the displayed image changes at a rate of 60 frames per second. Under certain conditions an image can become "stuck" for a time, so that when subsequent images are displayed, the stuck image is superimposed on those later images.

DETAILED DESCRIPTION

Introduction

Figure 1:
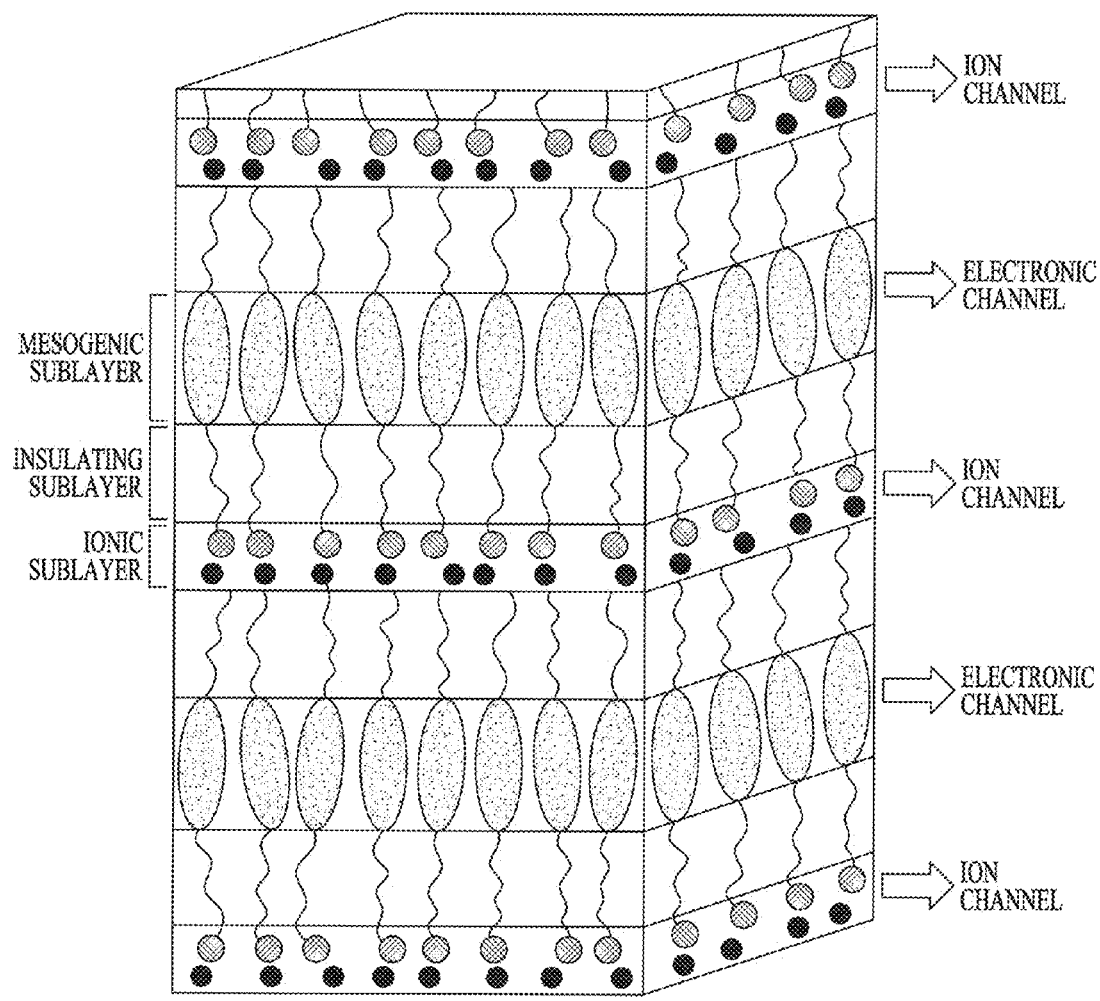
FIG. 1 is a schematic illustration of ionic liquid crystals (ILCs) combining both ionic and electronic conductivity in a nanostructured smectic phase. Spheres represent either cations or anions.

Multiple mechanisms can contribute to image sticking: charge accumulation at FLC-alignment layer interfaces, changes in director orientation at the alignment layer, changes of pretilt, and perhaps changes in director gliding behavior. The mechanism addressed here is the accumulation of electrical charge at the surfaces of the FLC layer in response to applied voltages. Typically, as judged by the appearance of image sticking, the time constant for growth and decay of accumulated surface charge ranges from minutes to hours. To combat this problem FLC displays generally show each image and its complement in sequence (i.e. dark pixels made bright and vice versa). This helps ensure that the average voltage experienced by each pixel is zero, thus no charge should accumulate (assuming that the charge accumulation time is long compared to the frame period). The disadvantage of this scheme, referred to here as dc-compensation (see Clark, N. A., C. Crandall, M. A. Handschy, M. R. Meadows, R. M. Malzbender, C. Park, and J. Z. Xue, FLC microdisplays. Ferroelectrics, 2000, 246, p. 97-110), is that illumination is often turned off during display of the image complement so that it is not seen by viewers; the resulting 50% duty cycle reduces the effective display brightness by half.

Duty cycle is defined as the proportion of time that the liquid crystal is driven so as to display the image. This is the maximum time that it is desirable to illuminate a display. For various reasons, it may not be desirable to illuminate the display for the entire period that the liquid crystal is driven so as to display the image.

Ionic liquids (ILs) are a special type of organic ionic compound, and they can be considered as molten (or liquid) ionic compounds at room temperature. Hence they are used not only as organic electrolytes for electrochemical cells, lithium ion batteries, fuel cells, capacitors, and solar cells,[1] but also as reaction media or catalysts for organic synthesis.[2]

Liquid crystals (LCs), as a new state of matter between liquid and solid, uniquely combine both order and mobility in the same material. The order leads to the anisotropy of LC molecules on both molecular and supermolecular levels, and the mobility enables LC molecules to respond easily with external stimuli. LCs self-assemble to macroscopically ordered structures which can be classified three major categories based on the orientational or positional orders of their molecules: nematic (N), smectic (Sm) and columnar (Col) phases. Nematic phases show only orientational order, smectic phases exhibit one-dimensional positional order and form two-dimensional layered structures, and columnar phases possess two-dimensional positional order and form tube-like one-dimensional structures. The most common smectic phases that rod-shaped LC molecules form are the smectic A (SmA) phase with the molecular long axis (i.e., director) normal to the layer plane, and the smectic C (SmC) phase with the director tilted with respect to the layer normal. The incorporation of chirality into the molecules forming SmC phases leads to SmC* phases, also called as ferroelectric liquid crystal (FLC) phases which possesses macroscopically polar order and in which the molecules can be switched between different ferroelectric states on a smectic cone upon the application of an external electric field.

Mesogenic compounds containing birefringent mesogenic groups and ionic moieties including ammonium,[11] imidazolium,[12] pyridinium,[13] pyrylium,[14] thiopyrylium,[14b, c] and dithiolium,[15] exist. These ionic liquid crystal (ILC) forming compounds have been found to exhibit various mesophases such as nematic, smectic and even columnar phases.

Note that ionic metallomesogens including a variety of transition metal complexes are also an important type of ILCs, which was found to exhibit various phases even including cubic phases.[8,16] Recently many complex ILCs bearing p-conjugated moieties have been reported to possess electronic charge transport properties in the columnar[17] and smectic[18] phases. Also it was found that anisotropic ionic conduction was significantly enhanced in the ionic LC systems compared to that in the isotropic liquid.[19] The enhanced transport properties of ILCs enable them more suitable for uses in a variety of devices such as field-effect transistors,[20] electroluminescence devices,[21] electrochromic devices,[22] actuators,[23] light-emitting diodes,[24] light-emitting electrochemical cells,[25] fuel cells and solar cells.[26]

Ferroelectric liquid crystals on silicon (FLCOS) microdisplay technology[27] are sometimes used because the sequential color images are better in quality and resolution than the color-filter triad images available from conventional liquid crystal on silicon (LCOS) microdisplay technology. However, device operation ions present in FLC mixtures may be trapped on surfaces to generate ghost images (i.e., image sticking) that will reduce image or display quality when the ghost images are superimposed on the subsequent normal images. To overcome this problem, a dc-balanced drive may be used in FLCOS microdisplays.

Under a dc-balanced drive mode, the FLCOS display has only 50% duty cycle which reduces the effective display brightness by half. If image sticking should be eliminated or reduced, the FLCOS displays could be operated under a dc-unbalanced mode with a duty cycle greater than 50%, thereby enabling brighter FLCOS microdisplays. There are many possible approaches to reduce or eliminate image sticking with respect to human vision. Two of these include: i) making ion-free FLC mixtures, ii) making FLC mixtures more conductive. The second approach is more feasible in practice than the first one.

It was recently discovered that doping conventional organic ionic compounds into FLC mixtures can significantly reduce image sticking, enabling FLCOS microdisplays to operate with a duty cycle of 75% (i.e., a 50% increase of brightness).[28]

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The terms "fluoroalkyl" and "fluoroalkoxy", as used herein, include fully and partially fluorinated alkyl and alkoxy groups, respectively.

The term "$(C_x-C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1-C_6)$perfluoroalkyl, more preferred is —$(C_1-C_3)$perfluoroalkyl, most preferred is —$CF_3$.

The term "$(C_x-C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1-C_6)$perfluoroalkylene, more preferred is —$(C_1-C_3)$perfluoroalkylene, most preferred is —$CF_2$—.

The term "amine" includes primary, secondary, and tertiary amines having, e.g., the formula $N(group)_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

A tetravalent phosphorus-centered cationic species, referred to as a "phosphonium" group herein, refers to a compound of structure $R_4P^+$, wherein the four R groups are independently selected.

A "boride" as the term is used herein refers to a tetravalent boron-centered anionic species. Examples include $BF_4^-$ (tetrafluoroborate), $BuBF_3^-$ (butyl trifluoroborate), and $DMBuBF_3^-$ (3,3-dimethylbutyl trifluoroborate).

The term "mesogenic", as used herein, refers to a compound that is capable of forming a liquid crystal.

A "dipolar aprotic solvent" as the term is used herein refers to organic solvents lacking OH groups. Examples include DMF, NMP, DMSO, and the like, as are well-known in the art.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used for the desired application. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

Description

Embodiments of the invention include novel ionic compounds having mesogenic properties, which themselves can form liquid crystal (LC) phases, or which can be used as dopants in LC mixtures. In various embodiments, novel ionic meosgenic materials are provided, which are useful as part of many devices, including field-effect transistors, electroluminescence devices, electrochromic devices, actuators, light-emitting diodes, light-emitting electrochemical cells, lithium ion batteries, fuel cells and solar cells, and displays, such as ferroelectric liquid crystal (FLC) dopants for higher duty cycle, brighter FLCOS microdisplays having improved anti-image sticking properties.

In various embodiments, the invention provides a mesogenic compound for a liquid crystal display, wherein the compound is of formula (I)

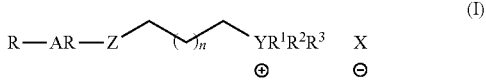

wherein
AR is a group of formula

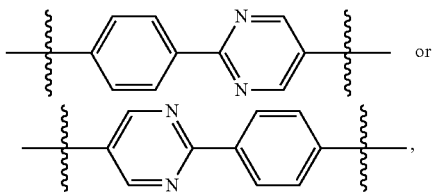

wherein a first wavy line indicates a point of attachment to R and a second wavy line indicates a point of attachment to Z;
R is a linear ($C_6$-$C_{16}$)alkyl, ($C_6$-$C_{16}$)fluoroalkyl, ($C_6$-$C_{16}$) alkoxy, ($C_6$-$C_{16}$)fluoroalkoxy, or a ($C_6$-$C_{16}$)alkyl-S(O)$_q$ group wherein q=0, 1 or 2;
n is 2 to 12;
$R^1$, $R^2$, and $R^3$ are each independently ($C_1$-$C_{16}$) alkyl or fluoroalkyl;
Y is N or P;
Z is O, S(O)$_q$, or CH$_2$ wherein q is 0, 1, or 2; and
X is an anion.

In various embodiments, the invention provides a liquid crystal display comprising a compound of formula (I). The liquid crystal display, such as a ferroelectric liquid crystal display, can have improved anti-image sticking properties; i.e., they exhibit reduced image sticking when compared to comparable liquid crystal displays lacking the ionic mesogenic compounds of the invention, either as the primary liquid crystal forming material(s), or as additives to known liquid crystal compositions.

In various embodiments, the invention provides a liquid crystal comprising a compound of formula (I). For example, the liquid crystal can be a ferroelectric liquid crystal. The compound of the invention can be a dopant in a liquid crystal formed of other materials, or can be the primary liquid crystal forming material.

In various embodiments, the invention provides a display device comprising an ionic mesogenic compound of formula (I) of the invention as a component of a liquid crystal, such as a ferroelectric liquid crystal. The display device can have reduced image sticking properties relative to a comparable device not comprising a compound of the invention.

Various embodiments of the invention are directed to ionic organic compounds that are mesogenic, i.e., that are capable of forming liquid crystals, such as ferroelectric liquid crystals; to methods of preparing such compounds; and to methods of using such compounds in manufacture of liquid crystal display devices, such as ferroelectric liquid crystal display devices. In various embodiments, compounds of the invention, which combine attributes of ionic liquids and liquid crystal forming materials, offer outstanding advantages. The ionic moieties provide for ionic conductivity of the system, and the mesogenic properties offer not only anisotropy of a liquid crystal composition comprising the compounds as well as electronic charge transport property (including both electrons and holes) in the system (FIG. 1).

Figure 2:
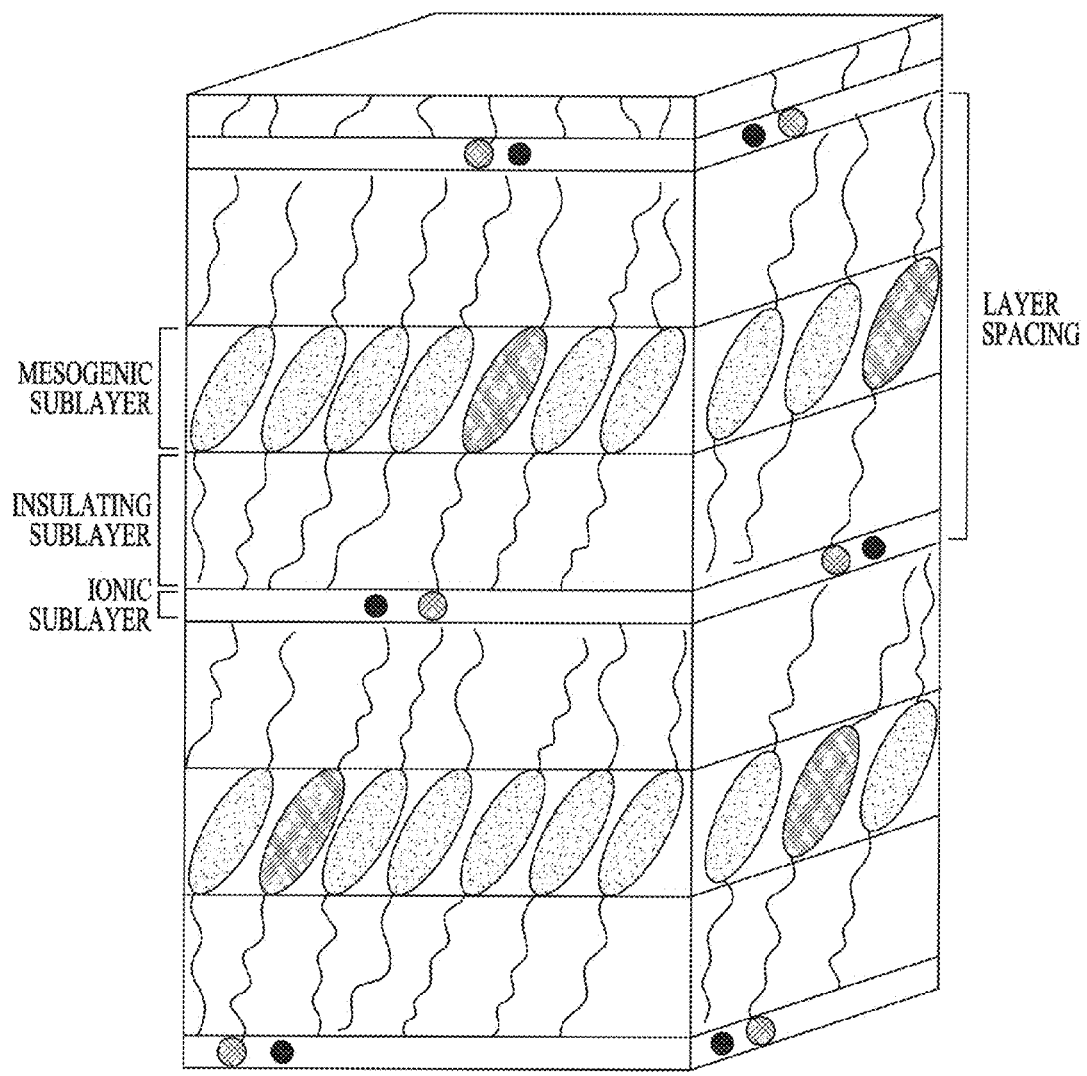
FIG. 2 is a schematic illustration of a FLC mixture including ILC dopants in a nanostructured SmC* phase. A ILC molecule consists of an aromatic core and two flexible aliphatic tails, with one tail bearing an ionic terminus located at smectic layer interfaces. Spheres represent either cations or anions.

ILC-forming materials of the invention comprising both mesogenic and ionic moieties can be used to form ferroelectric liquid crystals, or can be added as dopants to ferroelectric liquid crystal compositions of other materials. When added to known ferroelectric liquid crystal compositions, upon incorporation of compounds of the invention as dopants into FLC mixtures, the mesogenic compounds of the invention can be completely incorporated into FLC layer structures, with ionic moieties situated at smectic layer interfaces (FIG. 2). The stable and compatible combination not only provides the required conductivity for FLC mixtures along the smectic layer interfaces (i.e., narrow ionic channels) but also makes ILC dopants much more soluble in FLC mixtures than conventional ionic compounds. It was found that some ILCs can be added to the host FLC mixture up to 20 wt % without the appearance of phase separation (highly soluble in FLC mixtures). In such mixtures, phase separation and other superstructural changes are less likely to occur, and cells filled with them can have a long lifetimes. Thus, ILCs formed at least in part with mesogenic ionic compounds of the invention similar to FLC components can provide higher duty cycle, brighter ferroelectric liquid crystal on silicon (FLCOS) microdisplays.

Compounds in some embodiments can also be used as the primary liquid crystal forming material to produce ferroelectric liquid crystals, and displays incorporating the liquid crystals formed thereby, having improved anti-image sticking properties. In various embodiments, liquid crystals composed of materials including substantially only mesogenic ionic compounds of the invention, i.e., wherein the compounds are not dopants for art liquid crystal mixtures but are themselves the primary or only liquid crystal forming components, are provided. The ionic mesogenic compounds of the invention can provide advantages in formation of liquid crystal displays owing to their self-assembly to macroscopically ordered structures that facilitate both ionic and electronic conductivity.

In various embodiments, the invention provides an ionic mesogenic compound wherein the compound is of formula

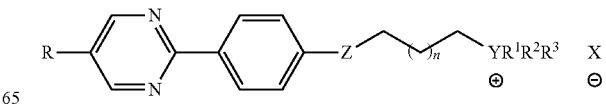

or of formula

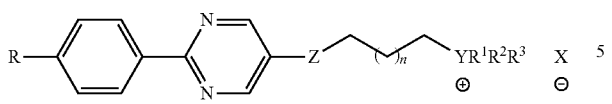

wherein

R is a linear $(C_6-C_{16})$alkyl, $(C_6-C_{16})$fluoroalkyl, $(C_6-C_{16})$alkoxy, $(C_6-C_{16})$fluoroalkoxy, or a $(C_6-C_{16})$alkyl-$S(O)_q$ group wherein q=0, 1 or 2;

n is 2 to 12;

$R^1$, $R^2$, and $R^3$ are each independently $(C_1-C_{16})$ alkyl or fluoroalkyl;

Y is N or P;

Z is O, $S(O)_q$, or $CH_2$ wherein q is 0, 1, or 2; and

X is an anion.

For example, the anion X can be an organic or an inorganic anion, such as a halide, a boride, an alkylsulfonate, a fluoroalkylsulfonate, a carboxylate, a phosphinate, perchlorate, or $PF_6^-$. More specifically, the halide can be chloride or iodide; or the boride can be $BF_4^-$, n-$BuBF_3^-$, or 3,3-dimethylbutyl$BF_3^-$; or the alkylsulfonate can be butylsulfonate or octylsulfonate; or the fluoroalkylsulfonate can be perfluorobutylsulfonate or perfluorooctylsulfonate; or the carboxylate can be trifluoroacetate; or the phosphinate can be bis-(2,4,4-trimethylpentyl)phosphinate.

In various embodiment, the invention provides a compound of formula (I) wherein Y is N (nitrogen), providing a cationic ammonium species. In other embodiments, Y can be P (phosphorus), providing a cationic phosphonium species.

In various embodiment, the invention provides a compound of formula (I) wherein R is a linear $(C_8-C_{12})$alkyl group. More specifically, R is n-$C_8H_{17}$, n-$C_{10}H_{21}$, or n-$C_{12}H_{25}$. Alternatively, R can be a partially or completely fluorinated linear $(C_8-C_{12})$alkyl group; for example R can be a $CF_3CF_2CF_2CF_2CH_2CH_2CH_2CH_2$ group. In other embodiments, R can be a $(C_6-C_{16})$alkoxy, or $(C_6-C_{16})$fluoroalkoxy group; for example R can be a n-octyloxy group, or R can be a perfluorooctyloxy group.

In various embodiment, the invention provides a compound of formula (I) wherein Z is O (oxygen). In other embodiments, Z can be S (thio), S(O) (sulfoxide), $S(O)_2$ (sulfone), or $CH_2$ (methylene).

In various embodiments, the invention provides a compound of formula (I) wherein $R^1$, $R^2$, and $R^3$ are each independently selected from the set consisting of ethyl, n-butyl, n-pentyl, n-hexyl, n-octyl, n-decyl, and n-dodecyl. More specifically, $R^1$, $R^2$, and $R^3$ can all be an identical alkyl selected from the set consisting of ethyl, n-butyl, n-pentyl, n-hexyl, n-octyl, n-decyl, and n-dodecyl.

In various embodiments, the compound can be any of the compounds of Table 1 or Table 2, below.

TABLE 1

Examples of Compounds of the Invention

| Compound # | Structure | |
|---|---|---|
| 1 | 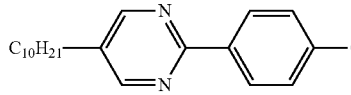 | I⁻ |
| 2 | 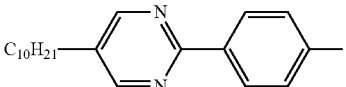 | BF₄⁻ |
| 3 | 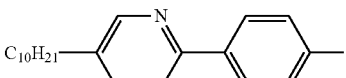 | Cl⁻ |
| 4 | 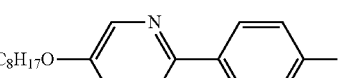 | BF4⁻ |
| 5 | 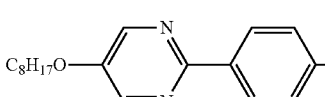 | I⁻ |
| 6 | 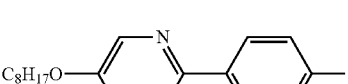 | Cl⁻ |
| 7 | 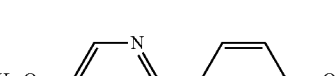 | C₄F₉SO₃⁻ |

TABLE 1-continued

Examples of Compounds of the Invention

| Compound # | Structure |
|---|---|
| 8 | $C_8H_{17}O$—[pyrimidine]—[phenyl]—O—$(CH_2)_4$—$NEt_3^{\oplus}$  $C_8F_{17}SO_3^-$ |
| 9 | $C_8H_{17}$—[pyrimidine]—[phenyl]—O—$(CH_2)_4$—$NEt_3^{\oplus}$  $I^-$ |
| 10 | $C_8H_{17}$—[pyrimidine]—[phenyl]—O—$(CH_2)_4$—$NEt_3^{\oplus}$  $BF_4^-$ |
| 11 | $C_8H_{17}$—[pyrimidine]—[phenyl]—O—$(CH_2)_4$—$NEt_3^{\oplus}$  $Cl^-$ |
| 12 | $C_8H_{17}$—[pyrimidine]—[phenyl]—O—$(CH_2)_4$—$NBu_3^{\oplus}$  $I^-$ |
| 13 | $C_8H_{17}$—[pyrimidine]—[phenyl]—O—$(CH_2)_4$—$NBu_3^{\oplus}$  $Cl^-$ |
| 14 | $C_8H_{17}$—[pyrimidine]—[phenyl]—O—$(CH_2)_4$—$NBu_3^{\oplus}$  $C_8F_{17}SO_3^-$ |
| 15 | $C_8H_{17}$—[pyrimidine]—[phenyl]—O—$(CH_2)_4$—$NBu_3^{\oplus}$  $BF_4^-$ |
| 16 | $C_8H_{17}$—[pyrimidine]—[phenyl]—O—$(CH_2)_4$—$NBu_3^{\oplus}$  $C_8H_{17}SO_3^-$ |
| 17 | $C_8H_{17}$—[pyrimidine]—[phenyl]—O—$(CH_2)_4$—$NBu_3^{\oplus}$  $C_4F_9SO_3^-$ |
| 18 | $C_{10}H_{21}$—[pyrimidine]—[phenyl]—O—$(CH_2)_{10}$—$NBu_3^{\oplus}$  $I^-$ |
| 19 | $C_{10}H_{21}$—[pyrimidine]—[phenyl]—O—$(CH_2)_{10}$—$NBu_3^{\oplus}$  $C_4F_9SO_3^-$ |
| 20 | $C_{10}H_{21}$—[pyrimidine]—[phenyl]—O—$(CH_2)_{10}$—$NBu_3^{\oplus}$  $BuBF_3^-$ |
| 21 | $C_{10}H_{21}$—[pyrimidine]—[phenyl]—O—$(CH_2)_{10}$—$NBu_3^{\oplus}$  $DMBuBF_3^-$ |

TABLE 1-continued
Examples of Compounds of the Invention
| Compound # | Structure |
|---|---|
| 22 | 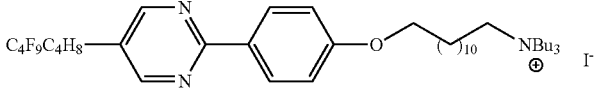 |
| 23 | 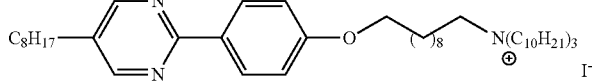 |
| 24 | 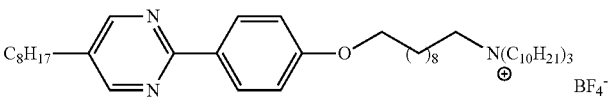 |
| 25 | 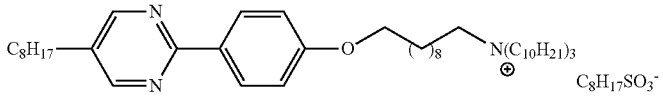 |
| 26 | 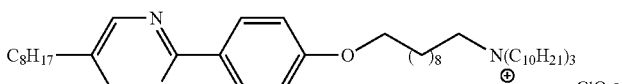 |
| 27 | 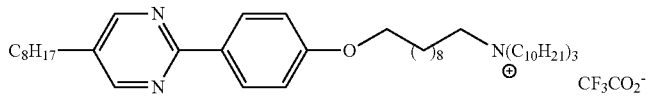 |
| 28 | 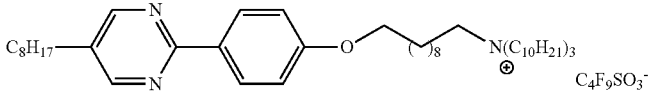 |
| 29 | 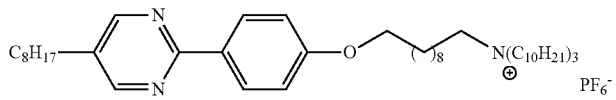 |
| 30 | 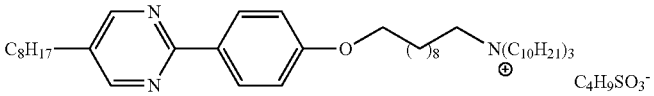 |
| 31 | 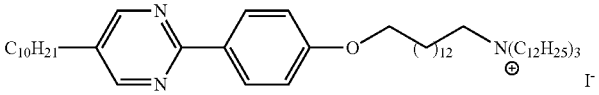 |
| 32 | 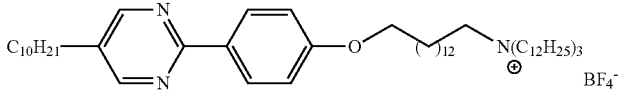 |
| 33 | 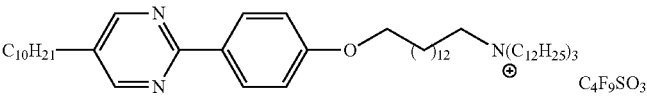 |
| 34 | 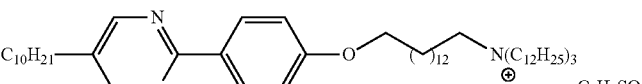 |

TABLE 1-continued

Examples of Compounds of the Invention

| Compound # | Structure |
|---|---|
| 35 | $C_{10}H_{21}$–pyrimidine–$C_6H_4$–O–$(CH_2)_{12}$–$\overset{\oplus}{N}(C_{12}H_{25})_3$  $PF_6^-$ |
| 36 | $C_{10}H_{21}$–pyrimidine–$C_6H_4$–O–$(CH_2)_{12}$–$\overset{\oplus}{N}(C_{12}H_{25})_3$  $CF_3CO_2^-$ |
| 37 | $C_8H_{17}$–pyrimidine–$C_6H_4$–O–$(CH_2)_4$–$\overset{\oplus}{N}(C_5H_{11})_3$  $I^-$ |
| 38 | $C_8H_{17}$–pyrimidine–$C_6H_4$–O–$(CH_2)_4$–$\overset{\oplus}{N}(C_5H_{11})_3$  $C_4F_9SO_3^-$ |
| 39 | $C_8H_{17}$–pyrimidine–$C_6H_4$–O–$(CH_2)_4$–$\overset{\oplus}{N}(C_6H_{13})_3$  $I^-$ |
| 40 | $C_8H_{17}$–pyrimidine–$C_6H_4$–O–$(CH_2)_4$–$\overset{\oplus}{N}(C_6H_{13})_3$  $C_4F_9SO_3^-$ |
| 41 | $C_8H_{17}$–pyrimidine–$C_6H_4$–O–$(CH_2)_4$–$\overset{\oplus}{N}Bu_3$  $OH^\ominus$ |
| 42 | $C_8H_{17}$–pyrimidine–$C_6H_4$–O–$(CH_2)_4$–$\overset{\oplus}{N}Bu_3$  with bis(2,4,4-trimethylpentyl)phosphinate anion |

All of the above compounds have been successfully synthesized and characterized by $^1$H and $^{13}$C NMR and LC-MS. Some of the exemplary compounds were further characterized by DSC and elemental analysis.

TABLE 2

Predictive Compounds of the Invention

| Compound # | Structure |
|---|---|
| P1 | $C_8H_{17}$–pyrimidine–$C_6H_4$–S–$(CH_2)_4$–$\overset{\oplus}{N}(C_4H_9)_3$  $C_4F_9SO_3^-$ |
| P2 | $C_8H_{17}$–pyrimidine–$C_6H_4$–$CH_2$–$(CH_2)_4$–$\overset{\oplus}{N}(C_4H_9)_3$  $C_4F_9SO_3^-$ |

TABLE 2-continued

Predictive Compounds of the Invention

Compound #

P3 — C8H17-pyrimidine-phenyl-O-(CH2)4-P(C4H9)3⊕  C4F9SO3⁻

P4 — C8H17-pyrimidine-phenyl-CH2-(CH2)4-P(C4H9)3⊕  C4F9SO3⁻

P5 — C12H25-pyrimidine-phenyl-S-(CH2)4-N(C4H9)3⊕  C4F9SO3⁻

P6 — C8H17-pyrimidine-phenyl-S(O)2-(CH2)4-N(C4H9)3⊕  C4F9SO3⁻

P7 — C8H17-pyrimidine-phenyl-S-(CH2)4-P(C4H9)3⊕  C4F9SO3⁻

P8 — C8H17S-pyrimidine-phenyl-O-(CH2)4-N(C4H9)3⊕  C4F9SO3⁻

P9 — C8H17S(O2)-pyrimidine-phenyl-O-(CH2)4-N(C4H9)3⊕  C4F9SO3⁻

Methods of Preparation of Ionic Mesogenic Compounds of the Invention

Compounds of the invention within the full scope of the generic structures disclosed herein, including specific compounds as listed above in Tables 1 and 2, can be prepared using subject matter disclosed herein in conjunction with the knowledge of the person of ordinary skill in the art of synthetic organic chemistry.

Scheme 1, below, provides a synthetic scheme that can be used for compounds wherein Z is oxygen.

Scheme 1: Synthetic Approach to Compounds of the Invention

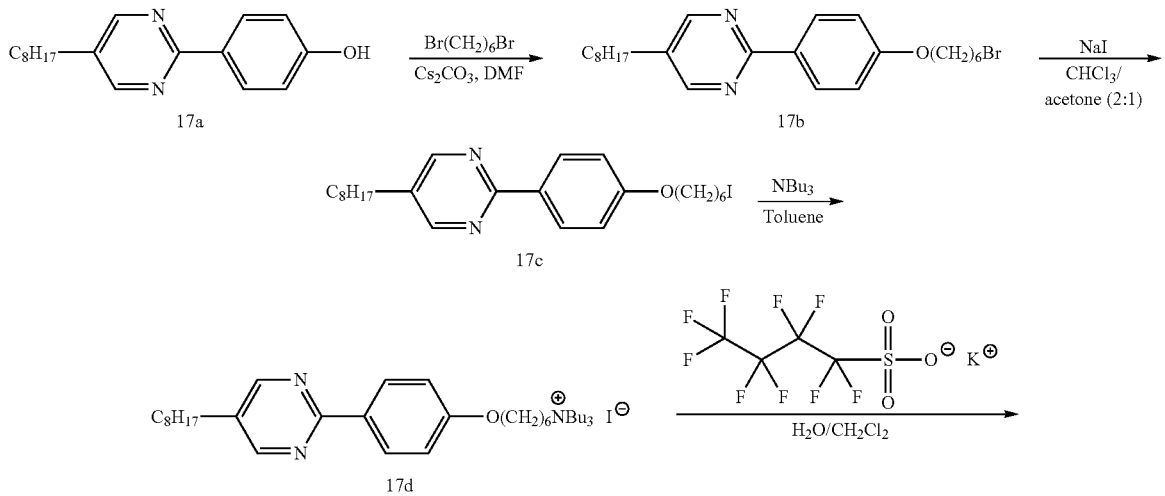

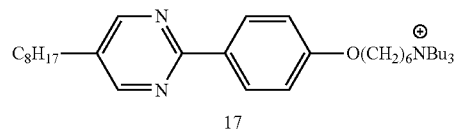
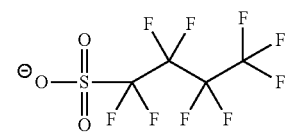

To a 500 mL round-bottom flask were added the phenol 17a (11.4 g, 40 mmol, 1.0 equiv), 1,6-dibromohexane (19.5 g, 80 mmol, 2.0 equiv), and $Cs_2CO_3$ (15.6 g, 48 mmol, 1.2 equiv) in 200 mL of DMF. The mixture was stirred overnight at rt and then heated to 80° C. for 1 h. To the mixture were added 200 mL of water and 200 mL of a 1:1 mixture of hexanes and EtOAc. The organic layer was separated and the aqueous layer was extracted with a 1:1 mixture of hexanes and EtOAc (3×100 mL). The organic layers were combined and dried over $MgSO_4$. Solvent removal and flash chromatography on silica gel gave a white solid of 15 g. Recrystallization of the solid from hexanes produced 12.5 g (69%) of 17b (very pure).

To a 500 mL round-bottom flask were added 17b (12.1 g, 27 mmol, 1.0 equiv) and 180 mL of $CHCl_3$. To this mixture was added NaI (12.1 g, 81 mmol, 3 equiv) in 90 mL of acetone. The mixture was heated at reflux for 15 min and then stirred overnight at rt. Filtration removed the solid. Solvent removal and flash chromatography on silica gel with an eluent (hexanes:EtOAc:$CH_2Cl_2$=80:10:10) gave 13.1 g of 17c as a while solid. LC-MS analysis of the material showed 99.7% purity of 17c with 0.3% of 17b. This material was directly used for the next reaction without further purification.

To a 100 mL round-bottom flask were added 17c (5.2 g, 10.5 mmol, 1.0 equiv) and $NBu_3$ (19.5 g, 105 mmol, 10 equiv) in 21 mL of toluene. The mixture was refluxed at 120° C. for 48 h. The heating and stifling were stopped and the solution was slowly cooled down to rt and kept at rt overnight. The solid precipitated. Filtration followed by washing with a mixture of hexanes/EtOAc afforded a crude product of 8 g. The crude product was recrystallized twice from 100 mL of EtOAc to afford 6.2 g (87%) of 17d as a white solid.

17d (0.4 g, 0.59 mmol, 1.0 equiv) was dissolved in 100 mL of $CH_2Cl_2$, and potassium perfluorobutylsulfonate (3.98 g, 11.77 mmol, 20 equiv) was dissolved in 150 mL of water. The $CH_2Cl_2$ solution was extracted with the above water solution (3×50 mL). Solvent removal gave 0.5 g of 17 as an oily product. This oil was dissolved with hexanes and put in a freezer (−20° C.) overnight. Two phases were separated. The top hexane layer was decanted and the bottom oil was dried overnight under vacuum to afford 0.42 g (84%) of 17 in high purity.

With suitable modifications, discussed below, this scheme can also guide the preparation of compounds wherein Z is other than oxygen, for example, when Z is methylene, thio, sulfoxide, or sulfone.

For preparation of the starting material, a suitable 2-halo-5-alkylpyrimidine, or the analogous 2-halo-5-fluoroalkylpyrimidine, 2-halo-5-alkoxypyrimidine, or 2-halo-5-fluoroalkoxypyrimidine, can be used in a para-coupling reaction with phenol to provide the pyrimidyl phenol, which can then be alkylated with a dihaloalkane to yield the phenolic ether. Activation of the terminal halide as an iodide by nucleophilic substitution with iodide ion, followed by alkylation with an amine, provides the ammonium species. Analogous alkylations with trialkylphosphines can provide the corresponding phosphonium species.

For compounds of formula (I) wherein Z is methylene can be prepared from a suitably para-substituted haloalkylbenzene, which is then coupled with the alkyl (or fluoroalkyl, alkoxy, or fluoroalkoxy)pyrimidine. Again, reaction of the chain-terminal halo group with an amine, or phosphine, produces the ammonium or phosphonium species respectively.

Scheme 2. Synthesis of the pyrimidyl phenols

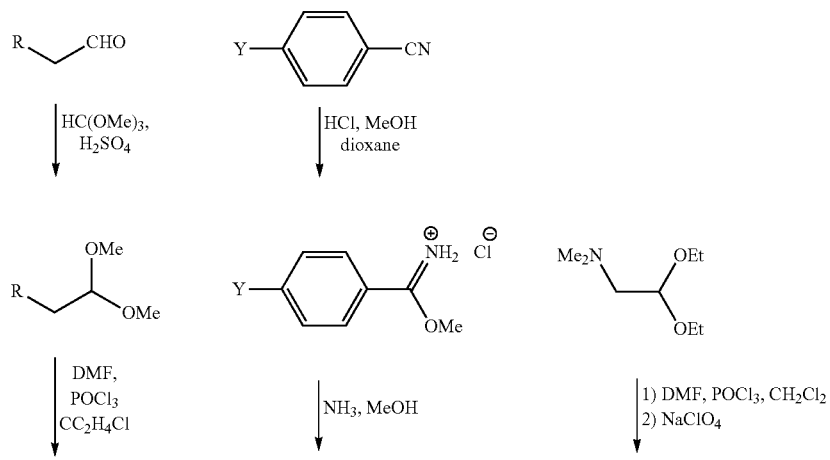

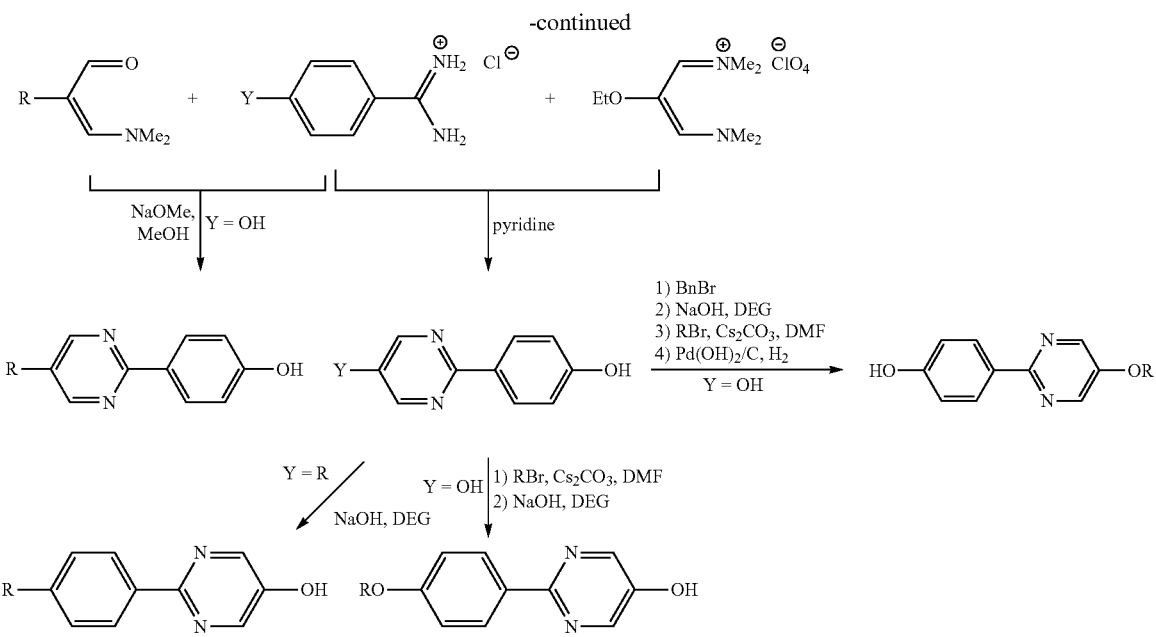

The starting pyrimidyl phenols were prepared from the readily available commercial chemicals (e.g., aliphatic aldehydes, 4-cyanophenol, and 4-alkylbenzonitrile) using the classic multi-step synthetic approaches as shown in Scheme 2. These intermediates could be also synthesized more efficiently using cross coupling reactions (e.g., Suzuki coupling, Negishi coupling, and Stille coupling) between the corresponding organometallics, which can be easily produced from 4-alkyl-1-bromobenzene or 4-alkoxyl-1-bromobenzene, and 5-bromo-2-iodopyrimidine in the presence of a transition metal catalyst (e.g., $Pd(PPh_3)_4$), followed by the transformation of the bromo unit to the hydroxyl group via oxidation of the produced boronic acid with hydrogen peroxide. The isomeric pyrimidyl phenols can be similarly synthesized using a proper protecting group (e.g., Y=OBn) (Scheme 3).

Scheme 3. Synthesis of the pyrimidyl phenols using cross coupling approaches

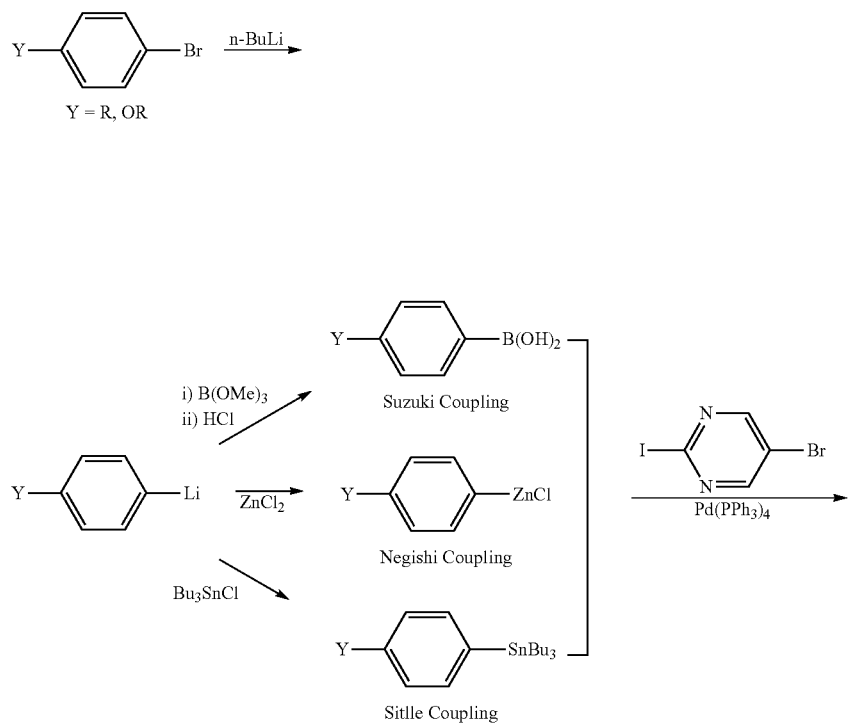

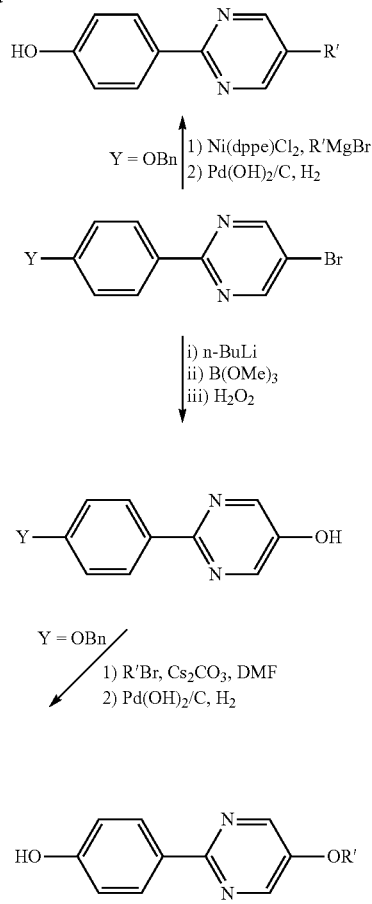

The pyrimidyl phenols can be similarly alkylated with a dihaloalkane to yield the phenolic ether. Activation of the terminal halide as an iodide by nucleophilic substitution with iodide ion, followed by alkylation with an amine, provides the ammonium species. Analogous alkylations with trialkylphosphines can provide the corresponding phosphonium species, respectively.

For preparation of the starting material, a suitable 2-halo-5-alkylpyrimidine, or the analogous 2-halo-5-fluoroalkylpyrimidine, 2-halo-5-alkoxypyrimidine, or 2-halo-5-fluoroalkoxypyrimidine, can be used in a para-coupling reaction with phenol to provide the pyrimidyl phenol, which can then be alkylated with a dihaloalkane to yield the phenolic ether. Activation of the terminal halide as an iodide by nucleophilic substitution with iodide ion, followed by alkylation with an amine, provides the ammonium species. Analogous alkylations with trialkylphosphines can provide the corresponding phosphonium species.

For compounds of formula (I) wherein Z is methylene can be prepared by transforming a suitable pyrimidyl phenol to its triflate, which is then coupled with the bromoalkane with a 9-BBN terminus in the presence of a palladium catalyst (Scheme 4). Activation of the terminal halide as an iodide by nucleophilic substitution with iodide ion, followed by alkylation with an amine, provides the ammonium species. Analogous alkylations with trialkylphosphines can provide the corresponding phosphonium species, respectively.

Scheme 4. The synthesis of compounds of formula (I) wherein Z is methylene:

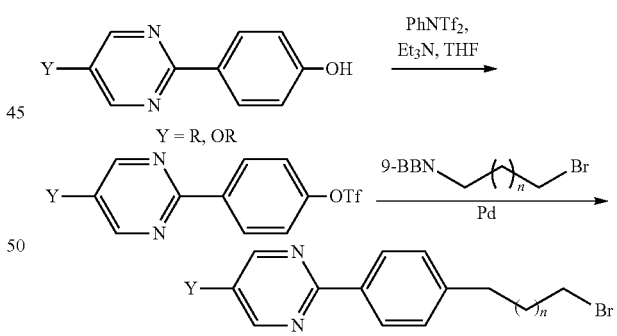

For compounds of formula (I) wherein Z is methylene can be prepared from a suitably para-substituted haloalkylbenzene, which is then coupled with the alkyl (or fluoroalkyl, alkoxy, or fluoroalkoxy)pyrimidine. Again, reaction of the chain-terminal halo group with an amine, phosphine, or sulfide, produces the ammonium, phosphonium, or sulfonium species respectively.

For species wherein Z is a sulfur group, thiophenol can be para-alkylated with the 2-halopyrimidine, the produce S-alkylated with a dihaloalkane as above, then reacted with the amine, phosphine, or sulfide. To prepare a sulfoxide or a sulfone from the sulfide, mild oxidation techniques such as are well known in the art can be employed.

Formation and Properties of Liquid Crystals

Figure 3A:
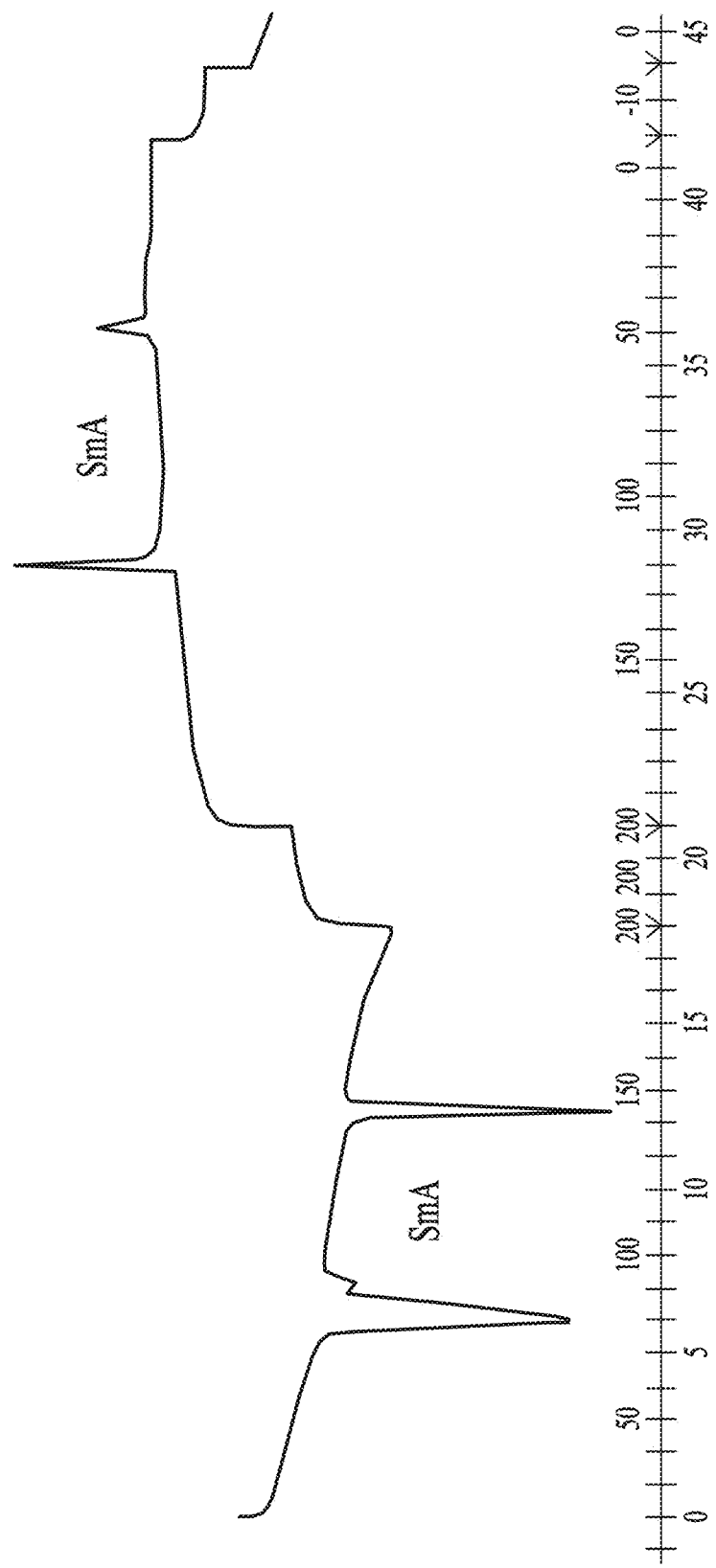
FIGS. 3A, 3B, 3C show DSC thermographs for representative compounds with small ionic terminus (a), mid-size ionic terminus (b), and large ioinic terminus (c).
Figure 3B:
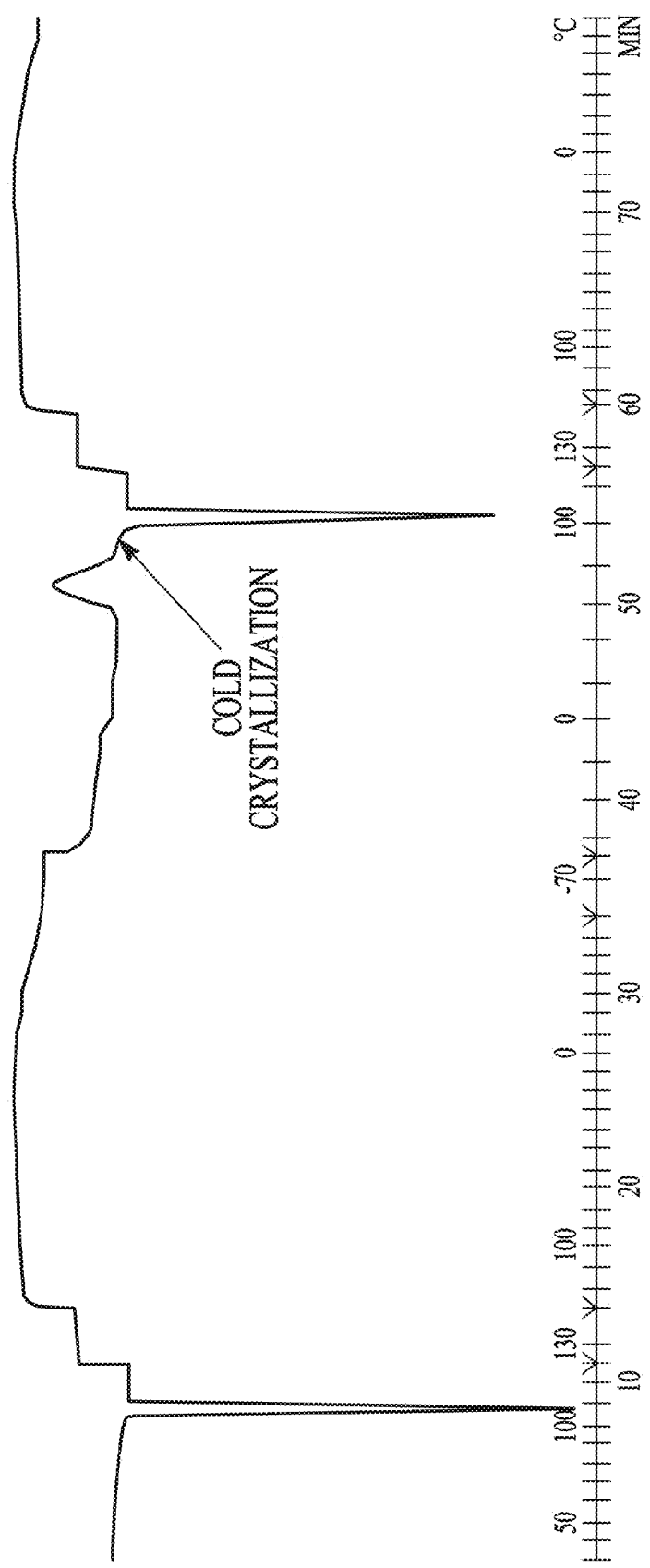
Figure 3C:
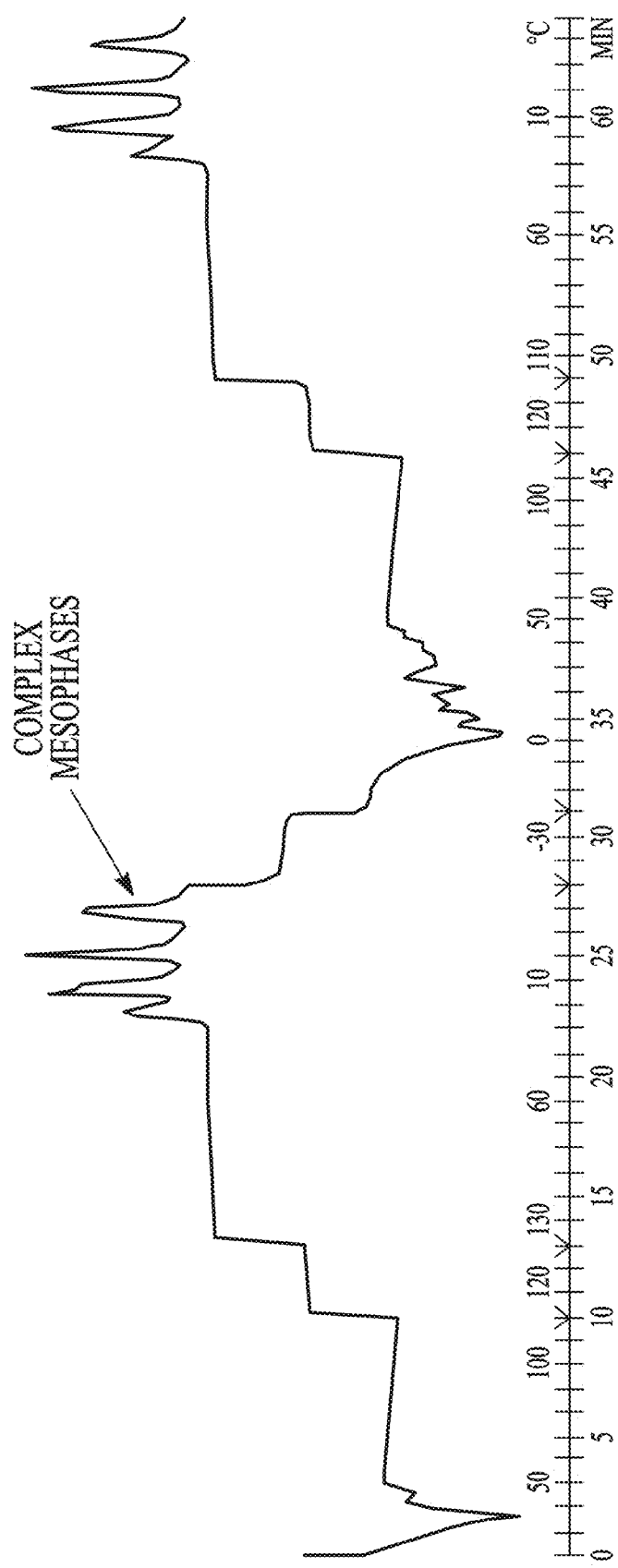

The liquid crystal properties of these compounds have been investigated by differential scanning calorimetry (DSC) and polarizing optical microscope (POM). Generally speaking, compounds with small ionic termini exhibit enantiotroic SmA phases, compounds with mid-size ionic termini don't show any mesophase, and compounds with large ionic termini show complex unidentified mesophases at low temperature (FIG. 3). For compounds with the same cations, the variation of anions has a significant effect on mesophases. For instance, compounds with a small-size chloride ion exhibit more mesophases than compounds with a large-size iodide ion.

General Information.

Cells for electro-optical investigations were filled with ILCs or ILC-doped FLC mixtures in their isotropic state via capillary force. A Nikon polarizing optical microscope (POM) equipped with a (Mettler FP82HT) hot stage and an oscilloscope was used to identify mesophases. The SmA phases were identified by observing ILC textures in both planar and homeotropic regions in cells filled with ILCs since the SmA phases exhibit birefringnent fan-shaped textures in planar regions and pseudo-isotropic textures (completely dark) in homeotropic regions. The phase transition temperatures and enthalpies were measured with a Mettler-Toledo DSC-822$^e$ differential scanning calorimeter (DSC) at 10 K·min$^{-1}$ during heating and cooling scans from −10 (or 200) to 200 (or −10)° C. Two sequential heating and cooling scans were normally performed. Materials for DSC and mixture formulations were weighed on a Mettler-Toledo AT261 DeltaRanger® balance.

The liquid crystal properties of these compounds have been investigated by differential scanning calorimetry (DSC) and polarizing optical microscope (POM). Generally speaking, compounds with small ionic termini exhibit enantiotroic SmA phases, compounds with mid-size ionic termini don't show any mesophase, and compounds with large ionic termini show complex unidentified mesophases at low temperature (FIG. 3). In (a) an enantiotropic SmA phase was identified; in (b) cold crystallization was observed during the second heating of a DSC scan followed by a crystalisotropic transition; and in (c) complex mesophases were observed in a temperature range of −30 to 26° C. during cooling. For compounds with the same cations, the variation of anions has a significant effect on mesophases. For instance, compounds with a small-size chloride ion exhibit more mesophases than compounds with a large-size iodide ion.

Image Sticking Investigations.

In addition to investigating the mesophases of these new ILCs, we have also examined the image sticking of FLC mixtures doped by these ILCs in low concentrations Like the conventional ionic compounds were previously studied, doping these new ILCs (0.01% to 1%) into FLC host mixtures significantly improve the image sticking of the host mixtures (FIG. 4).

Image sticking for compounds with small cations (e.g., $RNEt_3^+$) is worse than for those with mid- or large-size cations (e.g., $RNBu_3^+$ and $RN(C_{12}H_{25})_3^+$) probably owing to their low solubility in FLC hosts. Image sticking for compounds with inorganic anions is generally worse than for those with organic anions such as $C_4F_9SO_3^-$ and $CF_3CO_2^-$ with the exception of the inorganic anions such as $BF_4^-$ and $PF_6^-$. It was also found that 1 wt % of ILC dopants are much easier to generate phase separation than 0.1 wt % of ILC dopants. Therefore, a preferred dopant concentration in FLC hosts is not more than about 1%.

These new types of ILCs are structurally similar to other FLC components and can be completely incorporated into FLC layer structures. Thus they not only provide the required conductivity for FLC mixtures but also are more compatible with FLC components, more soluble in FLC mixtures, and less likely to crystallize from FLC mixtures than conventional ionic compounds, thereby enabling them as ideal dopant materials for higher duty cycle, brighter FLCOS microdisplays. This is strongly supported by reliability test results that ILCs are superior in overall performance to conventional ionic compounds.

The evaluation of image sticking was carried out using an automated image sticking analysis system having two principle components. The first component exposes the device to the test condition and acquires the image data for analysis. The second component uses the acquired images to determine the magnitude of the residual image across the display.

During the test, the device is exposed to the following conditions. First, the device is driven with white noise for one minute DC balanced while the LED illumination system is brought into thermal equilibrium. After the LED equilibrium period, the device is set to drive the desired non-DC balanced algorithm. Three images are acquired to define the pre-exposure state of the display. The three images are a bright state, a dark state, and a checkerboard pattern. The checkerboard pattern is the same pattern that is used during the exposure. After data for the initial state of the display is acquired, the device displays the checkerboard pattern for a five-minute dwell. This dwell is the test exposure condition. After the dwell, the device is switched to a dark state pattern and image data is collected. At the completion of the experiment sequence four images are available and used for the analysis step. Those images are an initial bright state, an initial checkerboard image, an initial dark state, and a post exposure dark state.

For each image acquisition step in the process camera integration time and the number of image averages are selectable. For a typical experiment, bright state integration times are 200 ms and dark state integration times are 1200 ms. Typically an average of 10 images is used for each acquisition.

Figures 4A, 4B, 4C:
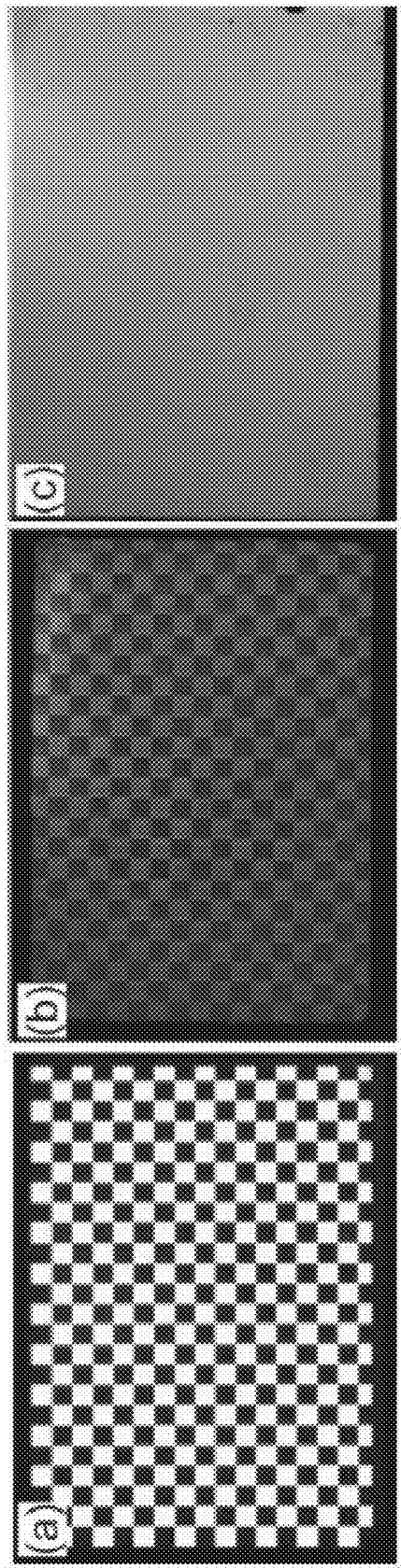
FIGS. 4A, 4B, 4C show a comparison between checkerboard patterns (a) and image sticking pictures for a FLC host mixture (b) and the same mixture doped with 0.1 wt % of an ILC dopant (c) upon the application a 9/3 checker drive for 5 min.

The image sticking analysis component uses the acquired images to determine the regional change in dark state brightness with respect to the pre-exposure dark state brightness. First, the acquired bright state image is used to compute any rotation in the active area of the display under test. Secondly, the pre-exposure checkerboard image is used to reference regions across the display for analysis after exposure. Typically, 176 analysis regions across the display are used. The checkerboard pitch used during the test exposure defines these analysis regions are as shown in FIG. 4. FIG. 4 shows a comparison between checkerboard patterns (a) and image sticking pictures for a FLC host mixture (b) and the same mixture doped with 0.1 wt % of an ILC dopant (c) upon the application a 9/3 checker drive for 5 min. Note that image sticking in (c) has been significantly improved by doping the ILC into the FLC host mixture in (b). In FIG. 4b, the image sticking value is about 30, wherein FIG. 4c, the value is close to 0.

In each analysis region, the software determines the difference in dark state brightness between regions in the checkerboard that were exposed bright and regions in the checkerboard that were exposed dark. Those differences are then compared to the display dark value in the analysis region prior to the test exposure. Consequently, for each of the 176 analysis regions, a value for image sticking as a percentage of the dark state is computed. Using the location data in conjunction with the image sticking magnitude the system can spatially resolve image-sticking variations across the panel. Additionally, basic statistics for the population of analysis regions are calculated to compare the performance across samples.

The resistivity of the FLC composition of various embodiments of the disclosed subject matter including the ionic mesogenic compound of the invention can be a factor in controlling the decrease in image sticking observed upon use of a composition of the disclosed subject matter compared to an art FLC composition lacking the ionic mesogenic compound. Although not wishing to be bound by theory, the inventors herein believe that the flow of electrical current through the FLC display device brought about by the presence of a suitable concentration of an ionic mesogenic compound, thus producing a suitable resistance in a specific FLC display device, may at least in part account for the favorable reduction in image sticking using the compositions and methods of the disclosed subject matter. The resistivity of any particular composition of the disclosed subject matter is a function, inter alia, of the concentration of the organic ions in the FLC composition, the mobility of the organic ions in the FLC composition, and possible phase separation (precipitation) of the organic ion pair compounds from the FLC composition.

For example, for a 1 cm² FLC cell adapted for use in a FLC display device, the capacitance of a generic polyimide alignment layer having a thickness of ~20 nm and a dielectric constant of ~4 is approximately 200 nC/cm². For switching rate $t_{SW}=1/720$ seconds (a typical FLCOS frame period) and eye image fusion rate $t_{vision}=1/30$ seconds this requires a cell resistance of about 14 kΩ to about 0.3 MΩ. For a typical FLC layer whose thickness is on the order of 1 μm, the resistivity of the FLC should correspondingly be in the range 140 MΩ·cm to about 3 GΩ·cm. In practice the $t_{vision}$ limit of $1/30^{th}$ seconds may be excessively stringent, i.e. it can be visually acceptable for image sticking to persist for a larger fraction of a second so that resistivities as large as 20 GΩ·cm may be acceptable. Accordingly, in such embodiments, the resistivity of the composition including the organic ion pair compound can be in the range of about 140 MΩ·cm to about 20 GΩ·cm, such that electrical resistance of the FLC composition in the above-described device can be within the range of about 14 kΩ to about 2 MΩ. The concentration of the organic ion pair compound in the FLC composition suitable to achieve such resistivities for the composition and resistances for the FLC display device as described can be about 0.005 wt % to about 0.5 wt %. More specifically, the concentration of the organic ion pair compound in the FLC composition can be about 0.05 wt % to about 0.15 wt %.

It is within ordinary skill to adjust a wt % of an organic ion pair compound in any particular FLC composition within these approximate ranges to achieve a suitable composition resistivity as defined above, such that the device displays a suitable resistance as defined above for a display device of a surface area of 1 cm2. It is within ordinary skill to calculate from the specified resistivity values the target resistance for a FLC display device of any area or layer thickness therefrom.

In various embodiments, the present disclosed subject matter provides a ferroelectric liquid crystal (FLC) display device comprising any of the ionic mesogenic compounds of the disclosed subject matter as described above. The display device can contain within the liquid crystal cell a ferroelectric liquid crystal display composition, for example Chisso CS1024, as are well known in the art, but containing as a dopant a ionic mesogenic compounds as described herein.

In various embodiments, the display can operate on a non-DC balanced algorithm with a greater than 50% duty cycle with a lower level of image sticking relative to a comparable display lacking the ionic mesogenic compound. The inventive FLC composition serves to reduce image sticking to a degree such that a neutralizing voltage need not be applied to relax the liquid crystal to its transmissive state. In various embodiments, the FLC display can be brighter when in operation than a comparable display lacking the organic ion pair compound and operating on a duty cycle of 50% or less would be. The enhanced brightness of FLC display devices available through the use of the inventive compositions is an outstanding advantage of the present disclosed subject matter.

In various embodiments, a FLC display device of the disclosed subject matter can comprise an ferroelectric liquid crystal layer having a composition wherein resistivity of the composition including the organic ion pair compound is in the range of about 140 MΩ·cm to about 20 GΩ·cm.

In various embodiments, a FLC display device of the disclosed subject matter can comprise an ferroelectric liquid crystal layer having a composition wherein resistivity of the composition including the organic ion pair compound is in the range of about 140 MΩ·cm to about 3 GΩ·cm.

In various embodiments of a FLC display device of the disclosed subject matter, image sticking persists for less than about $1/30^{th}$ of one second. In other embodiments, image sticking persists for less than about $1/12^{th}$ of one second.

Documents Cited 1) (a) Trulove, P. C.; Mantz, R. A. *Electrochemical Properties of Ionic Liquids*. In *Ionic Liquids in Synthesis*; Wasserscheid, P., Welton, T., Eds.; Wiley-VCH: Berlin, 2003; pp 103-126. (b) Ohno, H., Ed. *Electrochemical Aspects of Ionic Liquids*; Wiley: Hoboken, N.J., 2005. (c) Buzzeo, M. C.; Evans, R. G.; Compton, R. G. *Chem Phys Chem*. 2004, 5, 1106-1120. (d) Bonhôte, P.; Dias, A.-P.; Papageorgiou, N.; Kalyanasundaram, K.; Grätzel, M. *Inorg. Chem*. 1996, 35, 1168-1178. (e) Forsyth, S. A.; Pringle, J. M.; MacFarlane, D. R. *Aust. J. Chem*. 2004, 57, 113-119.

2) (a) Boon, J. A.; Levisky, J. A.; Pflug, J. L.; Wilkes, J. S. *J. Org. Chem*. 1986, 51, 480. (b) Cole, A. C.; Jensen, J. L.; Ntai, I.; Tran, K. L. T.; Weaver, K. J.; Forbes, D. C.; Davis, J. H. *J. Am. Chem. Soc*. 2002, 124, 5962-5963. (c) Fraga-Dubreuil, J.; Bazureau, J. P. *Tetrahedron Lett*. 2001, 42, 6097-6100. (d) Miao, W.; Chan, T. H. Org. Lett. 2003, 5, 5003-5005. (e) Anjaiah, S.; Chandrasekhar, S.; Gree, R. *Tetrahedron Lett*. 2004, 45, 569-571. (f) Lee, S. *Chem. Commun*. 2006, 1049-1063.

3) Tschierske, C.; Photinos, D. J. *J. Mater. Chem*. 2010, 20, 4263-4294.

4) *In Organic Photovoltaics: Mechanism, Mateials, and Devices*; Sun, S. S., Sariciftci, N. S., Eds., Taylor & Franics: Boca Raton. Fla., 2005.

5) Ma, J.; Li, Y.; White, T.; Urbas, A.; Li, Q. *Chem. Commun*. 2010, 3463-3465.

6) Chanishvili, A.; Chilaya, G.; Petriashvili, G.; Barberi, R.; Bartolino, R.; Cipparrone, G.; Mazzulla, A.; Oriol; L. *Adv. Mater*. 2004, 16, 791-795.

7) (a) Woltman, S. J.; Jay, G. D.; Crawford, G. P. Nat. Mater. 2007, 6, 929-938. (b) Woltman, S. J.; Jay, G. D.; Crawford, G. P. *Liquid Crystals: Frontiers in Biomedical Applications*; World Scientific Publishing Co. Pte. Ltd. Singapore 2007.

8) (a) K. Binnemans, *Chem. Rev.,* 2005, 105 (11), pp 4148-4204. (b) T. Kato, N. Mizoshita, K. Kishimoto, *Angew. Chem. Int. Ed.,* 2005, 45 (1), pp 38-68.

9) Vorländer, D. *Ber. Dtsch. Chem. Ges*. 1910, 43, 3120.

10) Knight, G. A.; Shaw, B. D. *J. Chem. Soc*. 1938, 682.

11) (a) Kokkinia, A.; Paleos, C. M.; Dais, P. *Mol. Cryst. Liq. Cryst.* 1990, 186, 239. (b) Tittarelli, F.; Masson, P.; Skoulios, A. *Liq. Cryst.* 1997, 22, 721. (c) Lu, L. D.; Weiss, R. G. *Langmuir* 1995, 11, 3630. (d) Lu, L.; Sharma, N.; Gowda, G. A. N.; Khetrapal, C. L.; Weiss, R. G. *Liq. Cryst.* 1997, 22, 23.

12) (a) Yoshizawa, H.; Mihara; Koide, N. *Mol. Cryst. Liq. Cryst.* 2004, 423, 61. (b) Yoshio, M.; Mukai, T.; Ohno, H.; Kato, T. *J. Am. Chem. Soc.* 2004, 126, 994. (c) Motoyanagi, J.; Fukushima, T.; Aida, T. *Chem. Commun.* 2005, 101. (d) Kouwer, P. H.; Swager, T. M. *J. Am. Chem. Soc.* 2007 129, 14042-14052.

13) (a) Boy, P.; Combellas, C.; Mathey, G.; Palacin, S.; Persoons, A.; Thiebault, A.; Verbiest, T. *Adv. Mater.* 1994, 6, 580. (b) Haramoto, Y.; Ujiie, S.; Nanasawa, M. *Liq. Cryst.* 1996, 21, 923. (c) Haramoto, Y.; Nanasawa, M.; Ujiie, S. *Liq. Cryst.* 2001, 28, 557. (d) Haramoto, Y.; Akiyami, Y.; Segawa, R.; Nanasawa, M.; Ujiie, S.; Holmes, A. B. *Bull. Chem. Soc. Jpn.* 1999, 72, 878. (e) Haramoto, Y.; Nanasawa, M.; Ujiie, S.; Holmes; A. B. *Mol. Cryst. Liq. Cryst.* 2000, 348, 129. (f) Haramoto, Y.; Kusakabe, Y.; Nanasawa, M.; Ujiie, S.; Mang, S.; Moratti, S. C.; Holmes, A. B. *Liq. Cryst.* 2000, 27, 263. (g) Haramoto, Y.; Akiyama, Y.; Segawa, R.; Ujiie, S.; Nanasawa, M. *Liq. Cryst.* 1998, 24, 877. (h) Haramoto, Y.; Akiyama, Y.; Segawa, R.; Ujiie, S.; Nanasawa, M. *J. Mater. Chem.* 1998, 8, 275. (i) Schadt, M.; Buchecker, R.; Muller, L. *Liq. Cryst.* 1989, 5, 293. (j) Buchecker, R.; Schadt, M. *Mol. Cryst. Liq. Cryst.* 1987, 149, 359. (k) Haramoto, Y.; Miyashita, T.; Nanasawa, M. Aoki, Y.; Nohira, H. *Liq. Cryst.* 2002, 29, 87. (l) Haristoy, D.; Tsiourvas, D. *Chem. Mater.* 2003, 15, 2079. (m) Navarro-Rodriguez, D.; Frere, Y.; Gramain, P.; Guillon, D.; Skoulios, A. *Liq. Cryst.* 1991, 9, 321. (n) Bravo-Grimaldi, E.; Navarro-Rodriguez, D.; Skoulios, A.; Guillon, D. *Liq. Cryst.* 1996, 20, 393. (o) Cui, L.; Sapagovas, V.; Lattermann, G. *Liq. Cryst.* 2002, 29, 1121.

14) (a) Veber, M.; Berruyer, G. *Liq. Cryst.* 2000, 27, 671. (b) Gionis, V.; Fugnitto, R.; Strzelecka, H. *Mol. Cryst. Liq. Cryst.* 1983, 95, 351. (c) Sigaud, G.; Hardouin, F.; Gasparoux, H.; Gionis, V.; Weber, M.; Strzelecka, H. *Mol. Cryst. Liq. Cryst.* 1983, 92, 217. (d) Strzelecka, H.; Jallabert, C.; Veber, M.; Davidson, P.; Levelut, A. M. *Mol. Cryst. Liq. Cryst.* 1988, 161, 395.

15) (a) Veber, M.; Jallabert, C.; Strzelecka, H.; Gionis, V.; Sigaud, G. *Mol. Cryst. Liq. Cryst.* 1986, 137, 373. (b) Strzelecka, H.; Jallabert, C.; Veber, M. *Mol. Cryst. Liq. Cryst.* 1988, 156, 355. (c) Davison, P.; Jallabert, C.; Levelut, A. M.; Strzelecka, H.; Veber, M. *Liq. Cryst.* 1988, 3, 133. (d) Veber, M.; Jallabert, C.; Strzelecka, H. *Synth. Comm.* 1987, 17, 693. (e) Veber, M.; Jallabert, C.; Strzelecka, H.; Jullien, O.; Davidson, P. *Liq. Cryst.* 1990, 8, 775. (f) Artzner, F.; Veber, M.; Clerc, M.; Levelut, A. M. *Liq. Cryst.* 1997, 23, 27.

16) Bruce, D. W.; Hudson, S. A. *J. Mater. Chem.*, 1994, 4, 479-486.

17) (a) Boden, N.; Bushby, R. J.; Clements, J.; Jesudason, M. V.; Knowles, P. F.; Williams, G. *Chem. Phys. Lett.* 1988, 152, 94-99. (b) Adam, D.; Closs, F.; Frey, T.; Funhoff, D.; Haarer, D.; Ringsdorf, H.; Schuhmacher, P.; Siemensmeyer, K. *Phys. Rev. Lett.* 1993, 70, 457-460. (c) vande Craats, A. M.; Warman, J. M.; Fechtenkötter, A.; Brand, J. D.; Harbison, M. A.; Müllen, K. *Adv. Mater.* 1999, 11, 1469-1472. (d) Breiby, D. W.; Bunk, O.; Pisula, W.; Sølling, T. I.; Tracz, A.; Pakula, T.; Müllen, K.; Nielsen, M. M. *J. Am. Chem. Soc.* 2005, 127, 11288-11293.

18) (a) Funahashi, M.; Hanna, J. *Appl. Phys. Lett.* 2000, 76, 2574-2576. (b) Funahashi, M.; Hanna, J. Adv. Mater. 2005, 17, 594-598. (c) Prehm, M.; Götz, G.; Bäuerle, P.; Liu, F.; Zeng, X.; Ungar, G.; Tschierske, C. *Angew. Chem., Int. Ed.* 2007, 46, 7856-7859. (d) Apperloo, J. J.; Janssen, R. A. J.; Malenfant, P. R. L.; Groenendaal, L.; Frechet, J. M. J. *J. Am. Chem. Soc.* 2000, 122, 7042-7051.

19) Yazaki, S.; Funahashi, M.; Kato, T. *J. Am. Chem. Soc.* 2008, 130, 13206-13207.

20) (a) Funahashi, M. *Polym. J.* 2009, 41, 459-469. (b) Funahashi, M.; Zhang, F.; Tamaoki, N. *Adv. Mater.* 2007, 19, 353-358. (c) Zhang, F.; Funahashi, M.; Tamaoki, N. *Org. Electron.* 2009, 10, 73-84. (d) Garnier, F.; Hajlaoui, R.; El Kassmi, A.; Horowitz, G.;
Laigre, L.; Porzio, W.; Armanini, M.; Provasoli, F. *Chem. Mater.* 1998, 10, 3334-3339. (e) Oikawa, K.; Monobe, H.; Nakayama, K.; Kimoto, T.; Tsuchiya, K.; Heinrich, B.; Guillon, D.; Shimizu, Y.; Yokoyama, M. *Adv. Mater.* 2007, 19, 1864-1868. (f) van Breemen, A. J. J. M.; Herwig, P. T.; Chlon, C. H. T.; Sweelssen, J.; Schoo, H. F. M.; Setayesh, S.; Hardeman, W. M.; Martin, C. A.; de Leeuw, D. M.; Valeton, J. J. P.; Bastiaansen, C. W. M.; Broer, D. J.; Popa-Merticaru, A. R.; Meskers, S. C. J. *J. Am. Chem. Soc.* 2006, 128, 2336-2345. (g) van de Craats, A. M.; Stutzmann, N.; Bunk, O.; Nielsen, M. M.; Watson, M.; Müllen, K. Chanzy, H. D.; Sirringhaus, H.; Friend, R. H. *Adv. Mater.* 2003, 15, 495-499. (h) Pisula, W.; Menon, A.; Stepputat, M. Lieberwirth, I.; Kolb, U.; Tracz, A.; Sirringhaus, H.; Pakula, T.; Müllen, K. *Adv. Mater.* 2005, 17, 684-689.

21) (a) Contoret, A. E. A.; Farrar, S. R.; Jackson, P. O.; Khan, S. M.; May, L.; O'Neill, M.; Nicholls, J. E.; Kelly, S. M.; Richards, G. J. *Adv. Mater.* 2000, 12, 971-974. (b) Aldred, M. P.; Contoret, A. E. A.; Farrar, S. R.; Kelly, S. M.; Mathieson, D.; O'Neill, M.; Tsoi, W. C.; Vlachos, P. *Adv. Mater.* 2005, 17, 1368-1372. (c) Kogo, K.; Goda, T.; Funahashi, M.; Hanna, J. *Appl. Phys. Lett.* 1998, 73, 1595-1597.

22) (a) Mortimer, R. J.; Dyer, A. L.; Reynolds, J. R. *Displays* 2006, 27, 2-18. (b) Onoda, M.; Nakayama, H.; Morita, S.; Yoshino, K. *J. Appl. Phys.* 1993, 73, 2859-2865. (c) Liou, G.-S.; Chang, C.-W. *Macromolecules* 2008, 41, 1667-1674. (d) Wu, C.-G.; Lu, M.-I. Chang, S.-J.; Wei, C.-S. *Adv. Funct. Mater* 2007, 17, 1063-1070. (e) Lu, W.; Fadeev, A. G.; Qi, B.; Smela, E.; Mattes, B. R. Ding, J.; Spinks, G. M.; Mazurkiewicz, J.; Zhou, D.; Wallace, G. G.; MacFarlane, D. R.; Forsyth, S. A.; Forsyth, M. *Science* 2002, 297, 983-987. (f) Argun, A. A.; Cirpan, A.; Reynolds, J. R. *Adv. Mater.* 2003, 15, 1338-1341. (g) Sapp, S. A.; Sotzing, G. A.;
Reynolds, J. R. *Chem. Mater.* 1998, 10, 2101-2108. (h) Sapp, S. A.; Sotzing, G. A.; Reddinger, J. L.; Reynolds, J. R. *Adv. Mater.* 1996, 8, 808-811. (i) Cutler, C. A.; Bouguettaya, M.; Reynolds, J. R. *Adv. Mater.* 2002, 14, 684-688.

23) (a) Smela, E. *Adv. Mater.* 2003, 15, 481-494. (b) Baughman, R. H. Synth. Met. 1996, 78, 339-353. (c) Jager, E. W. H.; Smela, E., Inganäs, O. *Science* 2000, 290, 1540-1545. (d) Carpi, F.; Gallone, G.; Galantini, F.; De Rossi, D. *Adv. Funct. Mater.* 2008, 18, 235-241.

24) (a) Yang, R.; Xu, Y.; Dang, X.-D.; Nguyen, T.-Q.; Cao, Y.; Bazan, G. C. *J. Am. Chem. Soc.* 2008, 130, 3282-3283. (b) Hoven, C., Yang, R.; Garcia, A.; Heeger, A. J.; Nguyen, T.-Q.; Bazan, G. C. *J. Am. Chem. Soc.* 2007, 129, 10976-10977.

25) (a) Pei, Q.; Yu, G.; Zhang, C.; Yang, Y.; Heeger, A. J. *Science* 1995, 269, 1086-1088. (b) Shao, Y.; Bazan, G. C.; Heeger, A. J. *Adv. Mater.* 2007, 19, 365-370. (c) Slinker, J. D.; DeFranco, J. A.; Jaquith, M. J.; Silveira, W. R.; Zhong, Y.-W.; Moran-Mirabal, J. M.; Craighead, H. G.; Abruna, H. D.; Marohn, J. A.; Malliaras, G. G. *Nat. Mater.* 2007, 6, 894-899. (d) Fang, J.; Matyba, P., Robinson, N. D.; Edman, L. *J. Am. Chem. Soc.* 2008, 130, 4562-4568. (e) Shin, J.-H.; Edman, L. *J. Am. Chem. Soc.* 2006, 128, 15568-15569. (f) Matyba, P.; Maturova, K.; Kemerink, M.; Robinson, N. D.; Edman, L. *Nat. Mater.* 2009, 8, 672-676.

26) (a) Qiao, Q.; Su, L.; Beck, J.; McLeskey, J. T., Jr. *J. Appl. Phys.* 2005, 98, 094906. (b) Yang, J.; Garcia, A.; Nguyen, T.-Q. *Appl. Phys. Lett.* 2007, 90, 103514.

27) Handschy, M. A.; Dallas, J. *SID Symposium Digest,* 2007, 38, 109-112.

28) (a) O'Callaghan, M.; Pecinovsky, C. U.S. Ser. No. 12/794,267, filed Jun. 4, 2010. (b) Pecinovsky, C.; Thurmes, W. Koprowski, B. U.S. patent Ser. Nos. 61/310,112, filed Mar. 3, 2010, and 13/007,297, filed Jan. 14, 2011.

All patents and publications, patent and non-patent, referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the claimed embodiments. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A mesogenic compound for a liquid crystal display, wherein the compound is of formula (I)

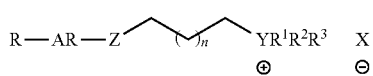

Wherein

R is a linear $(C_6-C_{16})$alkyl, $(C_6-C_{16})$fluoroalkyl, $(C_6-C_{16})$alkoxy, $(C_6-C_{16})$fluoroalkoxy, or a $(C_6-C_{16})$alkyl-$S(O)_q$ group wherein q=0, 1 or 2;

AR is a group of formula

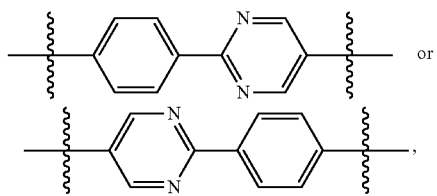

wherein a first wavy line indicates a point of attachment to R and a second wavy line indicates a point of attachment to Z;

n is 2 to 12;

$R^1$, $R^2$, and $R^3$ are each independently $(C_1-C_{16})$ alkyl or fluoroalkyl;

Y is N or P;

Z is O, $S(O)_q$, or $CH_2$ wherein q is 0, 1, or 2; and

X is an anion.

2. The compound of formula (I) of claim 1 wherein AR is

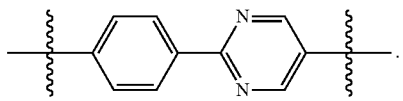

3. The compound of formula (I) of claim 1 wherein AR is

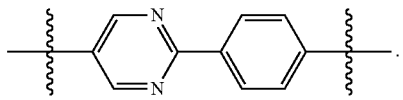 [SMILES: *c1ccc(-c2ncc(*)cn2)cc1 ; "."]

4. The compound of formula (I) claim 1 wherein X is a halide, a boride, an alkylsulfonate, a fluoroalkylsulfonate, a carboxylate, a phosphinate, perchlorate, or $PF_6^-$.

5. The compound of formula (I) of claim 4 wherein the halide is chloride or iodide; or the boride is $BF_4^-$, n-$BuBF_3^-$, or 3,3-dimethylbutyl$BF_3^-$; or the alkylsulfonate is butylsulfonate or octylsulfonate; or the fluoroalkylsulfonate is perfluorobutylsulfonate or perfluorooctylsulfonate; or the carboxylate is trifluoroacetate; or the phosphinate is bis-(2,4,4-trimethylpentyl)phosphinate.

6. The compound of formula (I) of claim 1 wherein Y is N.

7. The compound of formula (I) of claim 1 wherein R is a linear $(C_8-C_{12})$alkyl group.

8. The compound of formula (I) of claim 7 wherein R is n-$C_8H_{17}$, n-$C_{10}H_{21}$, or n-$C_{12}H_{25}$.

9. The compound of formula (I) of claim 1 wherein R is a partially or completely fluorinated linear $(C_8-C_{12})$alkyl group.

10. The compound of formula (I) of claim 9 wherein R is a $CF_3CF_2CF_2CF_2CH_2CH_2CH_2CH_2$ group.

11. The compound of formula (I) of claim 1 wherein R is a $(C_6-C_{16})$alkoxy or a $(C_6-C_{16})$ fluoroalkoxy group.

12. The compound of formula (I) of claim 1 wherein Z is O.

13. The compound of formula (I) of claim 1 wherein $R^1$, $R^2$, and $R^3$ are each independently selected from the set consisting of ethyl, n-butyl, n-pentyl, n-hexyl, n-octyl, n-decyl, and n-dodecyl group.

14. The compound of formula (I) of claim 12 wherein $R^1$, $R^2$, and $R^3$ are all an identical alkyl selected from the set consisting of ethyl, n-butyl, n-pentyl, n-hexyl, n-octyl, n-decyl, and n-dodecyl group.

15. The compound of formula (I) of claim 1 wherein the compound is any of the following:

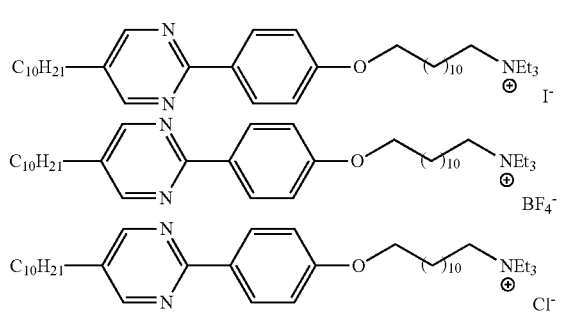

33
-continued
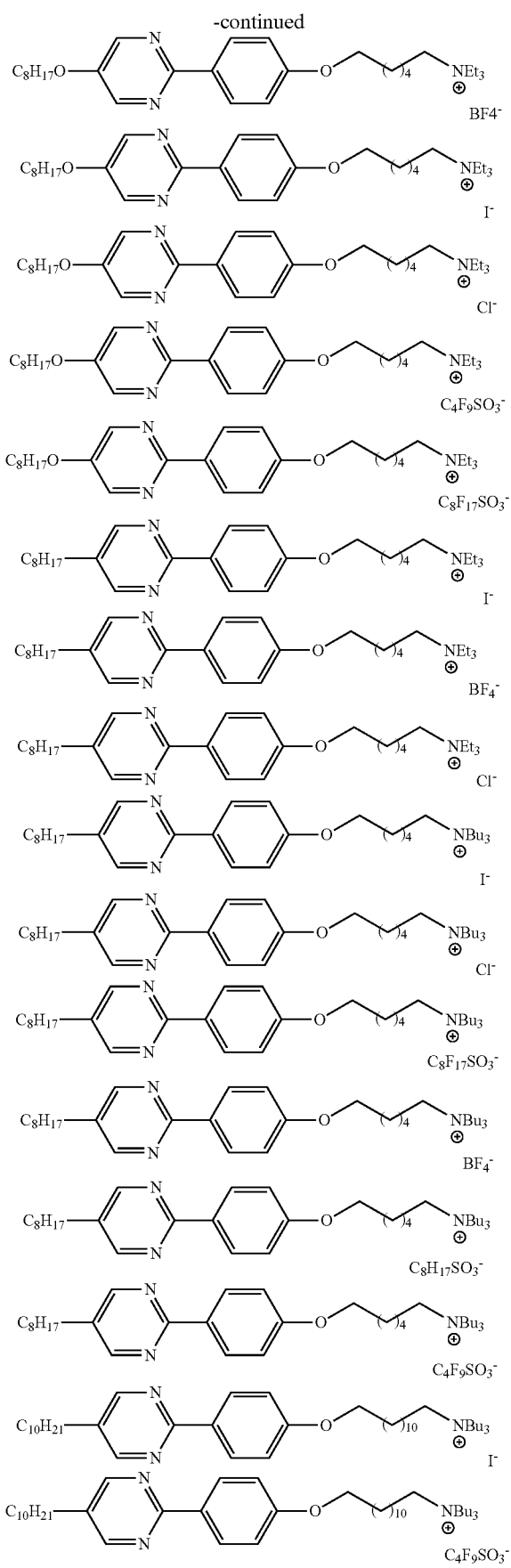
34
-continued
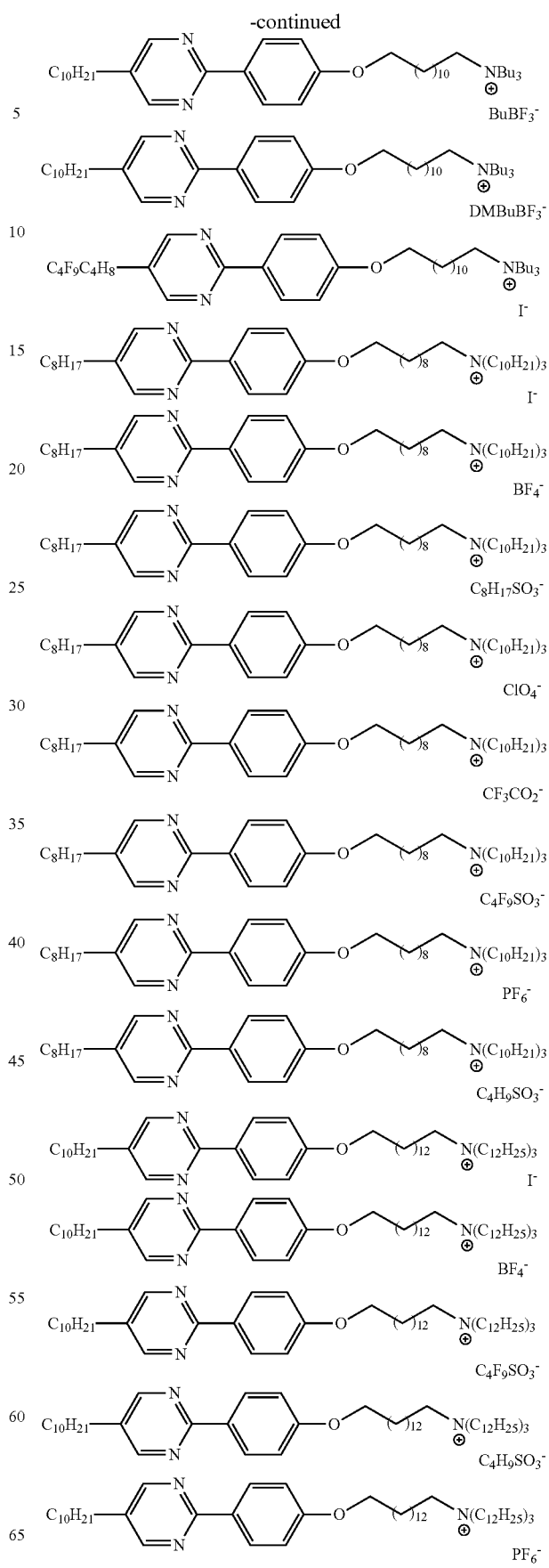

16. A liquid crystal composition comprising a compound of formula (I) A liquid crystal comprising a compound of formula (I)

$$R-AR-Z-(\phantom{x})_n-YR^1R^2R^3 \quad X \quad (I)$$
(with Y⊕ and X⊖)

Wherein
R is a linear $(C_6$-$C_{16})$alkyl, $(C_6$-$C_{16})$fluoroalkyl, $(C_6$-$C_{16})$ alkoxy, $(C_6$-$C_{16})$fluoroalkoxy, or a $(C_6$-$C_{16})$alkyl-$S(O)_q$ group wherein q=0, 1 or 2;
AR is a group of formula (structures shown)

wherein a first wavy line indicates a point of attachment to R and a second wavy line indicates a point of attachment to Z;
n is 2 to 12;
$R^1$, $R^2$, and $R^3$ are each independently $(C_1$-$C_{16})$ alkyl or fluoroalkyl;
Y is N or P;
Z is O, $S(O)_q$, or $CH_2$ wherein q is 0, 1, or 2; and
X is an anion.

17. The liquid crystal of claim 16 wherein AR is (structure shown)

18. The liquid crystal of claim 16 wherein AR is (structure shown)

19. The liquid crystal of claim 16 wherein X is a halide, a boride, an alkylsulfonate, a fluoroalkylsulfonate, a carboxylate, a phosphinate, perchlorate, or $PF_6$—.

20. The liquid crystal of claim 19 wherein the halide is chloride or iodide; or the boride is $BF_4^-$, n-$BuBF_3^-$, or 3,3-dimethylbutyl$BF_3^-$; or the alkylsulfonate is butylsulfonate or octylsulfonate; or the fluoroalkylsulfonate is perfluorobutylsulfonate or perfluorooctylsulfonoate; or the carboxylate is trifluoroacetate; or the phosphinate is bis-(2,4,4-trimethylpentyl)phosphinate.

21. The liquid crystal of claim 16 wherein Y is N.

22. The liquid crystal of claim 16 wherein R is a linear ($C_8$-$C_{12}$)alkyl group.

23. The liquid crystal of claim 16 wherein R is n-$C_8H_{17}$, n-$C_{10}H_{21}$, or n-$C_{12}H_{25}$.

24. The liquid crystal of claim 16 wherein R is a partially or completely fluorinated linear ($C_8$-$C_{12}$)alkyl group.

25. The liquid crystal of claim 24 wherein R is a $CF_3CF_2CF_2CF_2CH_2CH_2CH_2CH_2$ group.

26. The liquid crystal of claim 16 wherein R is a ($C_6$-$C_{16}$) alkoxy or a ($C_6$-$C_{16}$)fluoroalkoxy group.

27. The liquid crystal of claim 16 wherein Z is O.

28. The liquid crystal of claim 16 wherein $R^1$, $R^2$, and $R^3$ are each independently selected from the set consisting of ethyl, n-butyl, n-pentyl, n-hexyl, n-octyl, n-decyl, and n-dodecyl.

29. The liquid crystal of claim 16 wherein $R^1$, $R^2$, and $R^3$ are all an identical alkyl selected from the set consisting of ethyl, n-butyl, n-pentyl, n-hexyl, n-octyl, n-decyl, and n-dodecyl.

30. The liquid crystal of claim 16 wherein the compound of formula (I) is any of the following:

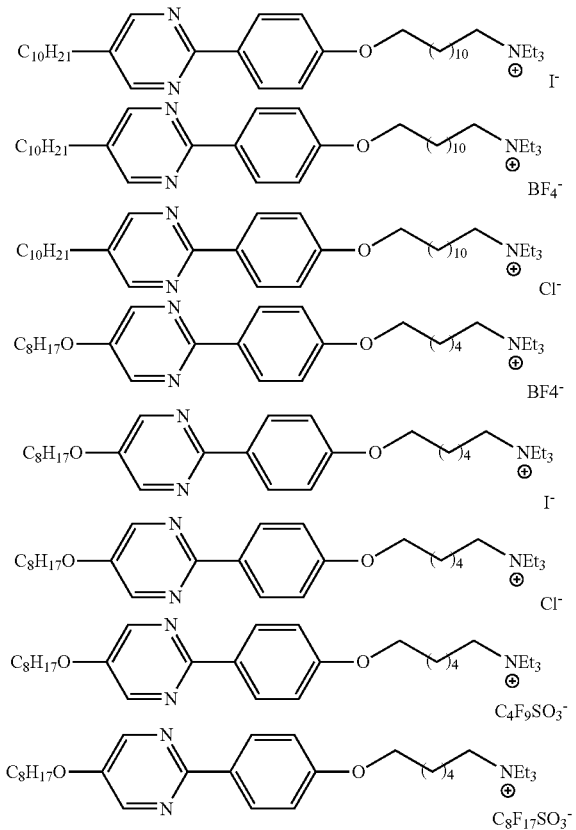

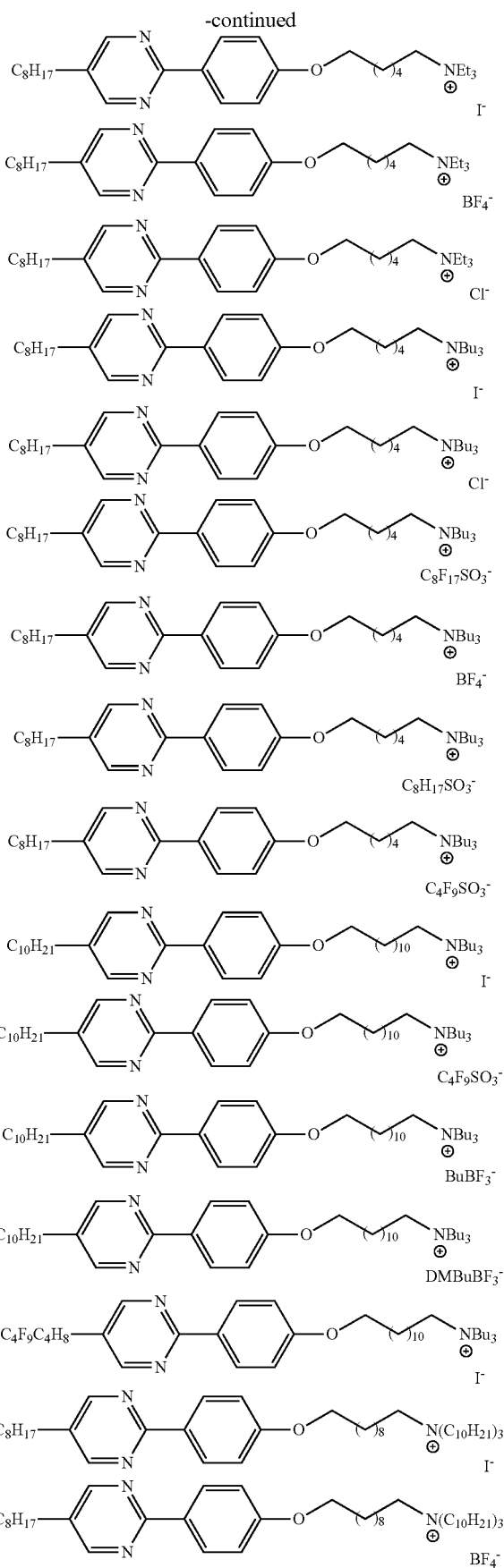

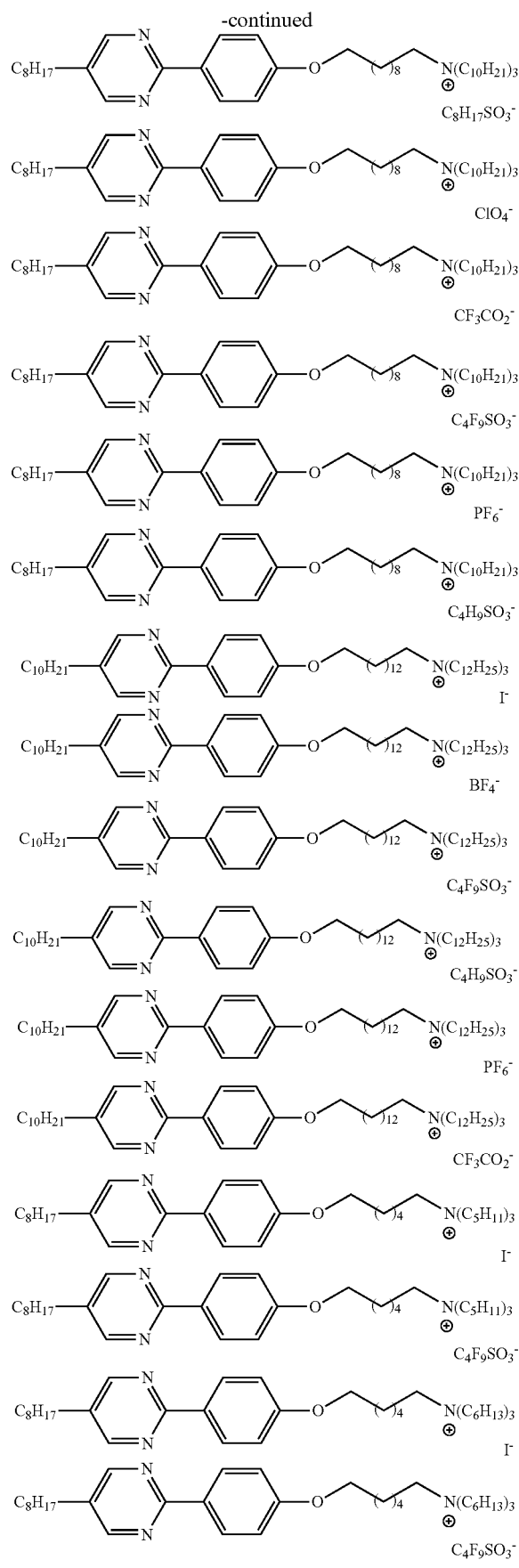

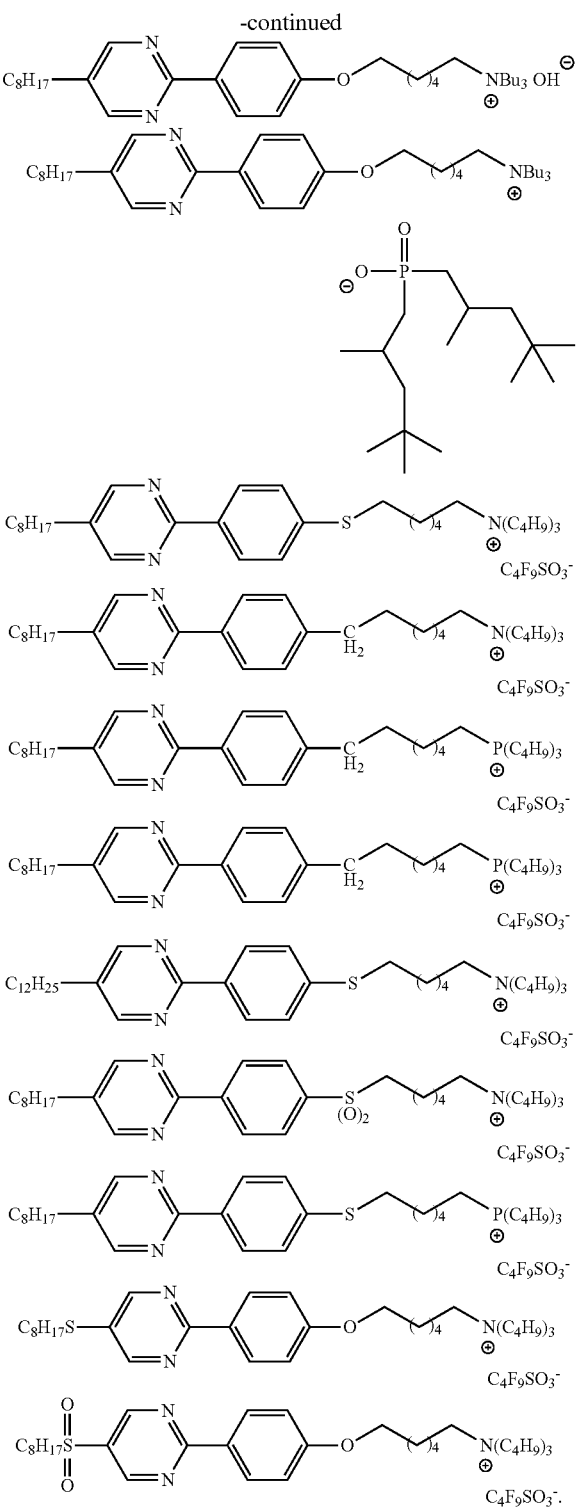

31. The liquid crystal of claim 16 wherein the liquid crystal is a ferroelectric liquid crystal.

32. A display device comprising the compound of claim 1 or the liquid crystal of claim 16.

33. The display device of claim 32 comprising a ferroelectric liquid crystal composition.

34. A method of preparing a liquid crystal display device on silicon comprising incorporating the liquid crystal composition of claim 16 into a liquid crystal display on silicon by disposing the liquid crystal composition, onto a silicon surface.

35. The method of claim 34 wherein the liquid crystal display device is a ferroelectric liquid crystal display device.

36. A method of preparing a compound of formula (I) of claim 1, comprising
   a) first, contacting a compound of formula R-AR-OH and a compound of formula Br—$(CH_2)_n$—Br, wherein R, AR, and n are as defined in claim 1, in a dipolar organic solvent in the presence of a base to provide a compound of formula R-AR-O—$(CH_2)_n$—Br;
   b) next, contacting the compound of formula R-AR-O—$(CH_2)_n$—Br and NaI in acetone solution to provide a compound of formula R-AR-O—$(CH_2)_n$—I; and,
   c) next, contacting the compound of formula R-AR-O—$(CH_2)_n$—I and $YR^1R^2R^3$, wherein Y, $R^1$, $R^2$, and $R^3$ are as defined in claim 1, to provide a compound of formula (I).

37. The method of claim 36 wherein AR is a group of formula

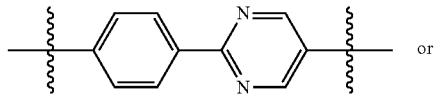 or

-continued

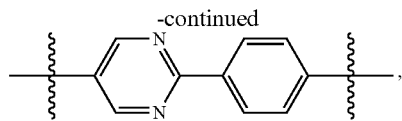, wherein a first wavy line indicates a point of attachment to R and a second wavy line indicates a point of attachment to Z.

38. The method of claim 36 wherein the dipolar aprotic solvent is DMF.

39. The method of claim 36 wherein the base is $CsCO_3$.

40. The method of claim 36 wherein Y is N.

41. The method of claim 36 wherein $R^1$, $R^2$, and $R^3$ are each independently selected from the set consisting of ethyl, n-butyl, n-pentyl, n-hexyl, n-octyl, n-decyl, and n-dodecyl.

42. The method of claim 41 wherein $R^1$, $R^2$, and $R^3$ are all identical.

43. A method of preparing a liquid crystal display device on silicon comprising,
   incorporating a compound of claim 1 into a liquid crystal display on silicon by disposing the compound in a liquid crystal onto a silicon surface.

44. The method of claim 34 wherein the liquid crystal display device is a ferroelectric liquid crystal display device.

45. The display device of claim 32 comprising a ferroelectric liquid crystal composition.

\* \* \* \* \*